(12) United States Patent
Wang et al.

(10) Patent No.: US 11,806,156 B2
(45) Date of Patent: Nov. 7, 2023

(54) METHOD AND SYSTEM FOR ADAPTIVE-SENSING OF ELECTRICAL CARDIAC SIGNALS

(71) Applicant: Pacesetter, Inc., Sylmar, CA (US)

(72) Inventors: Hanbiao Wang, Woodland Hills, CA (US); Xing Pei, Thousand Oaks, CA (US); Kyungmoo Ryu, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 4 days.

(21) Appl. No.: 17/192,171

(22) Filed: Mar. 4, 2021

(65) Prior Publication Data

US 2021/0330239 A1    Oct. 28, 2021

Related U.S. Application Data

(60) Provisional application No. 63/013,761, filed on Apr. 22, 2020.

(51) Int. Cl.
| | | |
|---|---|---|
| A61B 5/366 | (2021.01) | |
| A61B 5/352 | (2021.01) | |
| G16H 40/67 | (2018.01) | |
| A61B 5/355 | (2021.01) | |
| A61B 5/353 | (2021.01) | |

(52) U.S. Cl.
CPC .............. *A61B 5/366* (2021.01); *A61B 5/352* (2021.01); *A61B 5/353* (2021.01); *A61B 5/355* (2021.01); *G16H 40/67* (2018.01)

(58) Field of Classification Search
CPC ......... A61B 5/366; A61B 5/355; A61B 5/353; A61B 5/352; G16H 40/67
See application file for complete search history.

(56) References Cited

U.S. PATENT DOCUMENTS

| | | | |
|---|---|---|---|
| 7,245,965 B1* | 7/2007 | Pei ....................... | A61N 1/3622 607/18 |
| 8,275,457 B1* | 9/2012 | Fischell ................ | A61B 5/349 607/9 |
| 9,427,594 B1 | 8/2016 | Bornzin et al. | |
| 2016/0000382 A1* | 1/2016 | Jain ....................... | A61B 5/746 600/545 |
| 2019/0336026 A1* | 11/2019 | Dawoud ............... | A61N 1/3756 |
| 2019/0336032 A1* | 11/2019 | Gill ....................... | A61B 5/0031 |

(Continued)

*Primary Examiner* — Catherine M Voorhees
*Assistant Examiner* — Roland Dinga
(74) *Attorney, Agent, or Firm* — THE SMALL PATENT LAW GROUP LLC; Dean D. Small

(57) ABSTRACT

Computer implemented methods and systems for monitoring cardiac activity (CA) signals, for a series of beats, over first and second sensing channels having different first and second detection thresholds, respectively. The methods and systems also include analyzing the CA signals over the first and second sensing channels utilizing the first and second detection thresholds, respectively, during an event prediction window to detect a presence of sensed events. The methods and systems also include determining amplitudes of the sensed events detected. The methods and systems also include calculating at least one of an amplitude distribution or amplitude trend for the sensed events detected over the first and second channels and adjusting at least one of the first or second detection thresholds based on the at least one of the amplitude distribution or amplitude trend.

18 Claims, 10 Drawing Sheets

(56) References Cited

U.S. PATENT DOCUMENTS

2019/0336083 A1\* 11/2019 Gill ...................... A61B 5/7217
2020/0323458 A1\* 10/2020 Dawoud ................ A61B 5/363
2020/0376282 A1\* 12/2020 Bornzin ................ A61B 5/353

\* cited by examiner

METHOD AND SYSTEM FOR ADAPTIVE-SENSING OF ELECTRICAL CARDIAC SIGNALS

RELATED APPLICATION

The present application claims priority to U.S. Provisional Application No. 63/013,761, Titled "METHOD AND SYSTEM FOR ADAPTIVE-SENSING OF ELECTRICAL CARDIAC SIGNALS" which was filed on 22 Apr. 2020, the complete subject matter of which is expressly incorporated herein by reference in its entirety.

FIELD OF THE INVENTION

Embodiments herein relate generally to implantable medical devices, and more particularly to adaptive-sensing of cardiac activity signals in connection with identifying cardiac events.

BACKGROUND OF THE INVENTION

In a healthy heart, the sinoatrial node of the heart generates electrical pulses in a consistent and regulated fashion to regulate receiving and pumping blood in the heart's chambers. The electrical impulses propagate as activation wavefronts across the atria, the upper chambers of the heart, and cause cells of the atria to depolarize and contract, which forces blood from the atria to the ventricles, the lower chambers of the heart. The ventricles receive the blood from the atria, and the electrical impulse wavefront, after passing through the atrioventricular node and moving to the Purkinje system, moves to cells of the ventricles causing the ventricles to contract and pump the blood to the lungs and to the rest of the body.

Various aspects of cardiac activity (e.g., heart rate, arrhythmias) can be detected by measuring, recording, and analyzing cardiac activity signals. One way of measuring the cardiac activity signals involves attaching electrodes, externally to a patient's skin and sensing the electrical signals. Implantable systems, such as insertable cardiac monitors (ICMs) and subcutaneous implantable cardioverter-defibrillators (S-ICD), can be implanted under the skin with electrodes that sense subcutaneous electrical signals, which are indicative of cardiac activity.

The cardiac activity signals detected by the implanted electrodes are amplified, filtered, and rectified so that the signals have a common polarity. The rectified signal is then compared to a threshold voltage. When the rectified signal exceeds the threshold voltage, the detection circuitry of the system (e.g., ICM or S-ICD) determines that a sensed event (R-wave) has occurred.

For some known implantable systems, the threshold voltage compared to the rectified signal may be automatically adjusted based on the amplitude of a previous R-wave. For example, the threshold voltage for a subsequent beat may be set to a fixed percentage of the immediately previous R-wave. Challenges remain, however, because the amplitudes and morphologies of the rectified signal can significantly change as the physical contact between the electrodes and tissue changes. The electrode-tissue contact is dependent upon and changes based on implant location, physical activity, change in posture, sleep position and the like. Consequently, setting the threshold voltage to a fixed percentage of the prior R-wave may cause undersensing of signals-of-interest or oversensing of signals that are not necessary for analysis or the monitoring system's operation.

In addition to the above, it can be difficult to reliably identify particular sensed event characteristics within cardiac activity signals. For example, it can be difficult to detect P-waves or T-waves because the same subcutaneous electrodes also capture R-waves. The P-wave and the T-wave typically has a much smaller amplitude than the associated R-wave.

SUMMARY

In accordance with embodiments herein, a computer implemented method is provided. Under control of one or more processors configured with specific executable instructions, the method includes monitoring cardiac activity (CA) signals, for a series of beats, over first and second sensing channels having different first and second detection thresholds, respectively. The method also includes analyzing the CA signals over the first and second sensing channels utilizing the first and second detection thresholds, respectively, during an event prediction window to detect a presence of sensed events. The method also includes determining amplitudes of the sensed events detected. The method also includes calculating at least one of an amplitude distribution or amplitude trend for the sensed events detected over the first and second channels and adjusting at least one of the first or second detection thresholds based on the at least one of the amplitude distribution or amplitude trend.

Optionally, the first and second detection thresholds may represent a primary detection threshold and an upper guard threshold, respectively. The analyzing the CA signals may include determining whether the CA signals for a current beat of interest (BOI) exceed at least one of the primary detection threshold or the upper guard threshold. The upper guard threshold may be greater than the primary detection threshold.

Optionally, and responsive to the CA signals of the current BOI exceeding the upper guard threshold, the method may also include declaring that the sensed event is present within the current BOI and increasing at least one of the primary detection threshold or the upper guard threshold for a subsequent BOI.

Optionally, the increasing the at least one of the primary detection threshold or the upper guard threshold includes increasing the at least one of the primary detection threshold or the upper guard threshold based on an amplitude of the CA signals of the current BOI within the event prediction window.

Optionally, and responsive to the CA signals of the current BOI not exceeding the upper guard threshold but exceeding the primary detection threshold, the method may also include declaring that the sensed event is present within the current BOI and decreasing at least one of the primary detection threshold or the upper guard threshold for a subsequent BOI.

Optionally, the method also includes calculating at least one of an interval distribution or interval trend for events-of-interest from the CA signals and estimating a time of the event prediction window for detecting the sensed events based on the at least one of the interval distribution or interval trend.

Optionally, at least a third detection threshold may be added, wherein the first, second, and third detection thresholds are distributed within a sensitivity range. The analyzing the CA signals includes determining whether the CA signals for a current beat of interest (BOI) exceeds the first, second, or third detection thresholds. The method may also include increasing or decreasing one or more of the first, second, or third detection thresholds based on a total number of the first, second, or third detection thresholds being exceeded.

Optionally, the sensed event is at least one of an R-wave, a P-wave, or a T-wave.

Optionally, the method also includes processing the CA signals through first and second filtering circuits, wherein the first filtering circuit amplifies a first event-of-interest and the second filtering circuit amplifies a different second event-of-interest.

Optionally, the first filtering circuit selectively amplifies an R-wave or T-wave more than a P-wave and the second filtering circuit selectively amplifies the P-wave more than the R-wave or T-wave.

In accordance with embodiments herein, a system for detecting CA signals is provided. The system includes memory to store specific executable instructions and one or more processors configured to execute the specific executable instructions for monitoring cardiac activity (CA) signals, for a series of beats, over first and second sensing channels having different first and second detection thresholds, respectively; analyzing the CA signals over the first and second sensing channels utilizing the first and second detection thresholds, respectively, during an event prediction window to detect a presence of sensed events; determining amplitudes of the sensed events detected; calculating at least one of an amplitude distribution or amplitude trend for the sensed events detected over the first and second channels; and adjusting at least one of the first or second detection thresholds based on the at least one of the amplitude distribution or amplitude trend.

Optionally, the first and second detection thresholds represent a primary detection threshold and an upper guard threshold, respectively. The analyzing the CA signals includes determining whether the CA signals for a current beat of interest (BOI) exceed at least one of the primary detection threshold or the upper guard threshold, wherein the upper guard threshold being greater than the primary detection threshold.

Optionally, when the CA signals of the current BOI exceed the upper guard threshold, the one or more processors are configured to declare that the sensed event is present within the current BOI and increase at least one of the primary detection threshold or the upper guard threshold for a subsequent BOI.

Optionally, the one or more processors are further configured to increase the at least one of the primary detection threshold or the upper guard threshold based on the amplitude of the CA signals of the current BOI within the event prediction window.

Optionally, when the CA signals of the current BOI do not exceed the upper guard threshold but do exceed the primary detection threshold, the one or more processors are configured to: declare that the sensed event is present within the current BOI and decrease at least one of the primary detection threshold or the upper guard threshold for a subsequent BOI.

Optionally, the one or more processors are configured to: calculate at least one of an interval distribution or interval trend for events-of-interest from the CA signals and estimate a time of the event prediction window for detecting the sensed events based on the at least one of the interval distribution or interval trend.

Optionally, at least a third detection threshold is added, wherein the first, second, and third detection thresholds are distributed within a sensitivity range. The one or more processors are configured to: determine whether the CA signals for a current beat of interest (BOI) exceed the first, second, or third detection thresholds and increase or decrease one or more of the first, second, or third detection thresholds based on a total number of the first, second, or third detection thresholds that are exceeded.

Optionally, the sensed event is at least one of an R-wave, a P-wave, or a T-wave.

Optionally, the system also includes first and second filtering circuits within the first and second sensing channels. The first filtering circuit is configured to amplify a first event-of-interest and the second filtering circuit is configured to amplify a different second event-of-interest. The first and second events of interest represent different first and second sensed events.

Optionally, the first filtering circuit selectively amplifies an R-wave or T-wave more than a P-wave and the second filtering circuit selectively amplifies the P-wave more than the R-wave or the T-wave.

DETAILED DESCRIPTION

Figure 1:
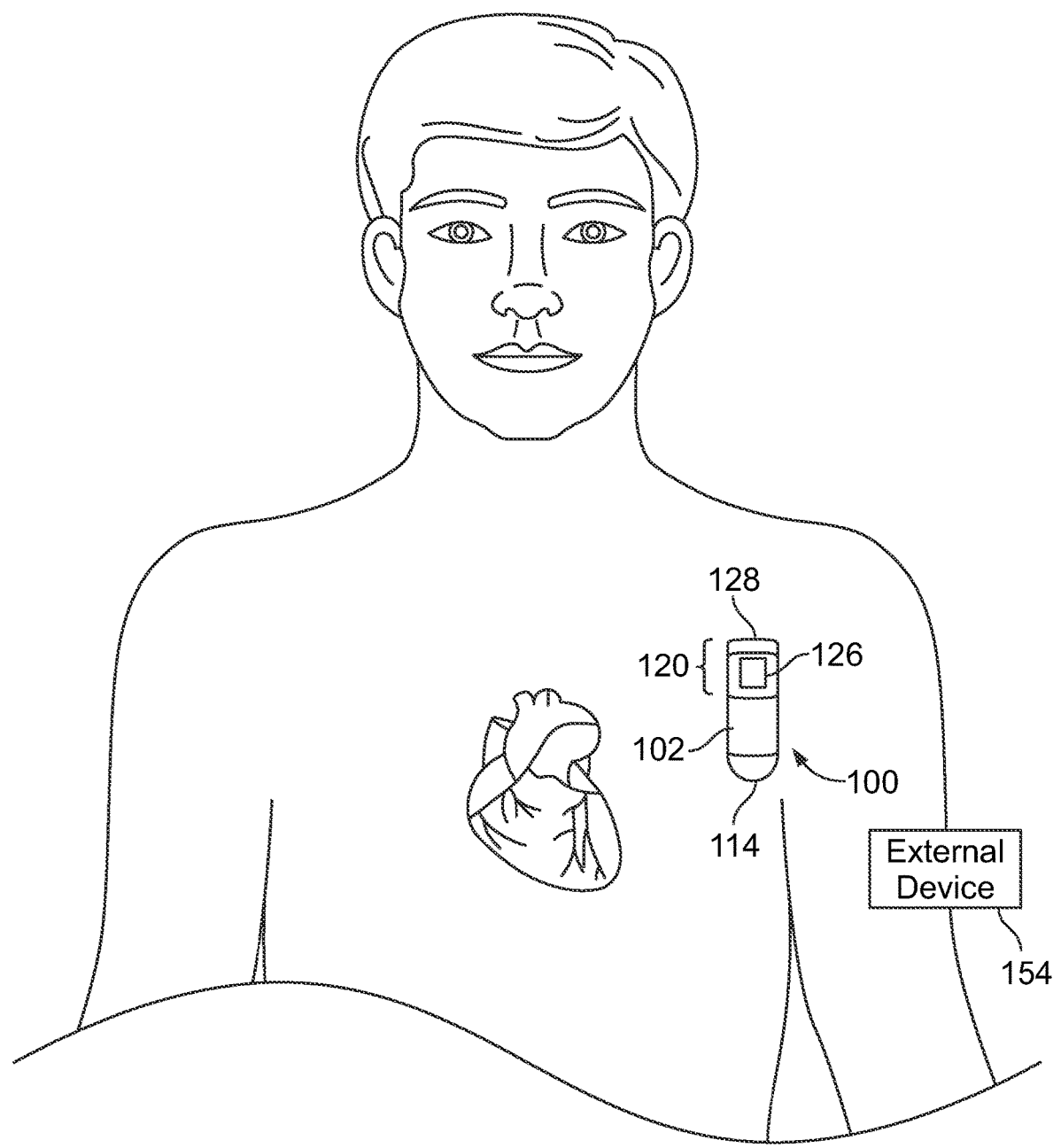
FIG. 1 illustrates an implantable cardiac monitoring device (ICM) intended for subcutaneous implantation at a site near the heart in accordance with embodiments herein.

Embodiments set forth herein include methods and systems for adaptive-sensing of cardiac activity. The methods and systems may utilize one or more sensing channels of an implantable medical device, such as an insertable cardiac monitor (ICM) or a subcutaneous implantable cardio-defibrillator (S-ICD), to detect and analyze sensed events. A sensed event may correspond to the cardiac activity (CA) signals of a single beat, an R-wave, P-wave, T-wave, and the like. Embodiments determine and monitor characteristics of sensed events, such as an amplitude, a morphology of the CA signals for the single beat or sensed event, a noise floor, and one or more event intervals (e.g., P-P, P-R, R-T, and R-R intervals).

Embodiments may monitor the characteristics of sensed events, trends of the characteristics, and a background noise level (or noise floor) to predict when the next sensed event should occur. This time period is referred to herein as an "event prediction window." Embodiments may also adjust the threshold settings for the event prediction window. For example, embodiments may predict when the peak of an R-wave of a CA signal for the next beat will occur, designate a time period for observing the amplitude, and adjust multiple thresholds to be applied during the event prediction window. The adjustments (e.g., amount of increase or decrease) may be based on the amplitude of one or more prior beats. For example, the adjustment may be based on an amplitude distribution and/or amplitude trend in which each of the amplitude distribution and the amplitude trend are a function of amplitudes and/or morphologies from prior beats.

In particular embodiments, the adaptive-sensing process can be implemented using a limited coherent combination of multiple sensing channels. For example, a main or primary sensing channel may be configured to perform full range signal sensing. Other sensing channels may be used collectively for adjusting sensitivity thresholds. For example, two or more sensing channels may each apply a different threshold to the CA signals at the event prediction window. Yet other sensing channels may be configured to perform narrow range signal sensing, such as in connection with detecting P-waves or T-waves or other characteristics-of-interest.

Particular embodiments may utilize multiple detection thresholds (e.g., two, three, four, five, six, or more thresholds). The CA signals for one beat may be analyzed over multiple sensing channels to determine whether the CA signals exceed the multiple detection thresholds. Based on a number of the detection thresholds (for various sensing channels and/or beats) that were exceeded, the detection thresholds may be increased, decreased, or unchanged for the next beat. For example, thresholds are exceeded for two or three channels over 4-5 beats, at least some of the detection thresholds are increased for a subsequent beat. If only one or none of the sensing channel thresholds are exceeded for a select number of beats, at least some of the detection thresholds may be decreased for a subsequent beat. In some embodiments, the amount of increase or decrease in the detection thresholds may be a function of the amplitude of the CA signals detected during a series of prior beats. In other embodiments, however, the amount of increase or decrease in the detection thresholds may not be a function of the amplitude of the CA signals.

Embodiments may be implemented in connection with one or more implantable medical devices (IMDs). Non-limiting examples of IMDs include one or more of implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like.

Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

Additionally or alternatively, the IMD may be a leadless cardiac monitor (ICM) that includes one or more structural and/or functional aspects of the device(s) described in U.S. patent application Ser. No. 15/084,373, filed Mar. 29, 2016, entitled, "METHOD AND SYSTEM TO DISCRIMINATE RHYTHM PATTERNS IN CARDIAC ACTIVITY," which is expressly incorporated herein by reference.

Embodiments may be implemented in connection with one or more passive IMDs (PIMDs). Non-limiting examples of PIMDs may include passive wireless sensors used by themselves, or incorporated into or used in conjunction with other implantable medical devices (IMDs) such as cardiac monitoring devices, pacemakers, cardioverters, cardiac rhythm management devices, defibrillators, neurostimulators, leadless monitoring devices, leadless pacemakers, replacement valves, shunts, grafts, drug elution devices, blood glucose monitoring systems, orthopedic implants, and the like. For example, the PIMD may include one or more structural and/or functional aspects of the device(s) described in U.S. Pat. No. 9,265,428 entitled "Implantable Wireless Sensor", U.S. Pat. No. 8,278,941 entitled "Strain Monitoring System and Apparatus", U.S. Pat. No. 8,026,729 entitled "System and Apparatus for In-Vivo Assessment of Relative Position of an Implant", U.S. Pat. No. 8,870,787 entitled "Ventricular Shunt System and Method", and U.S. Pat. No. 9,653,926 entitled "Physical Property Sensor with Active Electronic Circuit and Wireless Power and Data Transmission", which are all hereby incorporated by reference in their respective entireties.

All references, including publications, patent applications and patents, cited herein are hereby incorporated by reference to the same extent as if each reference were individually and specifically indicated to be incorporated by reference and were set forth in its entirety herein.

I. Terms and Abbreviations

The terms "cardiac activity signal", "cardiac activity signals", "CA signal" and "CA signals" (collectively "CA signals") are used interchangeably throughout to refer to an analog or digital electrical signal recorded by two or more electrodes, where the electrical signals are indicative of cardiac activity. The cardiac activity may be normal/healthy or abnormal/arrhythmic. An example of CA signals includes EGM signals.

The term "COI" refers to a character of interest within CA signals. Nonlimiting examples of characters of interest include an R-wave, P-wave, or T-wave. A character of interest may correspond to a peak of an individual R-wave, an average or median P, R or T-wave peak and the like.

The terms "beat" and "cardiac event" are used interchangeably and refer to both normal or abnormal events.

The terms "normal" and "sinus" are used to refer to events, features, and characteristics of, or appropriate to, a heart's healthy or normal functioning.

The terms "abnormal," or "arrhythmic" are used to refer to events, features, and characteristics of, or appropriate to, an un-healthy or abnormal functioning of the heart.

The term "real-time" refers to a time frame contemporaneous with a normal or abnormal episode occurrences. For example, a real-time process or operation would occur during or immediately after (e.g., within minutes or seconds after) a cardiac event, a series of cardiac events, an arrhythmia episode, and the like.

The term "adaptive", as used in connection with a sensitivity profile, sensitivity limit, sensitivity level or other sensing parameters, refers to an ability of the processes herein to modify the value of sensitivity and/or sensing parameters or thresholds based on features within the CA signals. The sensitivity profile parameters may include refractory period, start sensitivity, decay delay, sensitivity limit, slope of sensitivity decay, etc.

The term "sensitivity level", as used herein, refers to a threshold that an input CA signal must exceed for an implantable device to identify a PQRST complex feature of interest (e.g., P-wave, T-wave, R-wave). As one non-limiting example, software may be implemented using a programmed sensitivity level to declare an R-wave to be detected when the input CA signal exceeds the current programmed sensitivity level. In response, the software declares a device documented feature (e.g., R-wave) marker. The sensitivity level may be defined in various manners based on the nature of the CA signals. For example, when the CA signals measure electrical activity in terms of millivolts, the sensitivity level represents a millivolt threshold. For example, when a cardiac beat with a 0.14 mV amplitude is sensed by device hardware, an R-wave may be detected when the current sensitivity level is programmed to 0.1 mV. However, when the sensitivity level is programmed to 0.15 mV or above, a cardiac beat with an amplitude of 0.14 mV will not be detected as an R-wave. Embodiments herein may determine an adaptive sensitivity limit and sensitivity profile for the sensitivity level.

Particular embodiments may utilize a number of thresholds for identifying a sensed event (e.g., R-wave) and adjusting the thresholds for a subsequent beat. Thresholds may include a primary detection threshold, upper guard thresholds, lower guard thresholds, etc.

The term "distribution" (e.g., amplitude distribution) refers to a range of values that a characteristic-of-interest may have or is likely to have. The range may be based on prior CA signal data. For example, the values may correlate to amplitudes detected from the CA signals over a series of beats. The distribution may represent a probability that an amplitude will have a certain value within the range. For example, the probability that an amplitude will have a value at a center of the range will be greater than the probability that an amplitude will have a value at an end of the range. Embodiments may determine how much to increase or decrease detection thresholds to be used during an event prediction window based on the amplitude distribution from a prior series of beats.

The term "trend" refers to a direction of change, rate of change, or lack of change of a characteristic-of-interest over time. The trend is based on prior CA signals over a series of beats. For example, an "amplitude trend" indicates whether a series of amplitudes are increasing, decreasing, or remaining the same over time, and/or optionally the rate of increase, rate of decrease. Embodiments may determine how much to increase or decrease detection thresholds during an event prediction window based on the amplitude trend from a prior series of beats.

II. System Overview

FIG. 1 illustrates an implantable cardiac monitoring device (ICM) 100 intended for subcutaneous implantation at a site near the heart. The ICM 100 includes a pair of spaced-apart sense electrodes 114, 126 positioned with respect to a housing 102. The sense electrodes 114, 126 provide for detection of electrogram (EGM) signals (e.g., far-field EGM signals). Numerous configurations of electrode arrangements are possible. For example, the electrode 114 may be located on a distal end of the ICM 100, while the electrode 126 is located on a proximal side of the ICM 100. Additionally or alternatively, electrodes 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 114 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the AF detection algorithm described herein, a loop memory for temporary storage of CA data, a device memory for long-term storage of CA data upon certain triggering events, such as AF detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor—tissue interface. The ICM 100 may be configured to be activated by the patient or automatically activated, in connection with recording subcutaneous CA signals.

The ICM 100 may sense subcutaneous CA signals, process the CA signals to detect arrhythmias and if an arrhythmia is detected, automatically records the CA signals in memory for subsequent transmission to an external device 154. The CA signal processing and AF detection is provided for, at least in part, by algorithms embodied in or implemented by the microprocessor. The ICM 100 includes one or more processors and memory that stores program instructions directing the processors to implement AF detection utilizing an on-board R-R interval irregularity (ORI) process that analyzes cardiac activity signals collected over one or more sensing channels.

Figure 2:
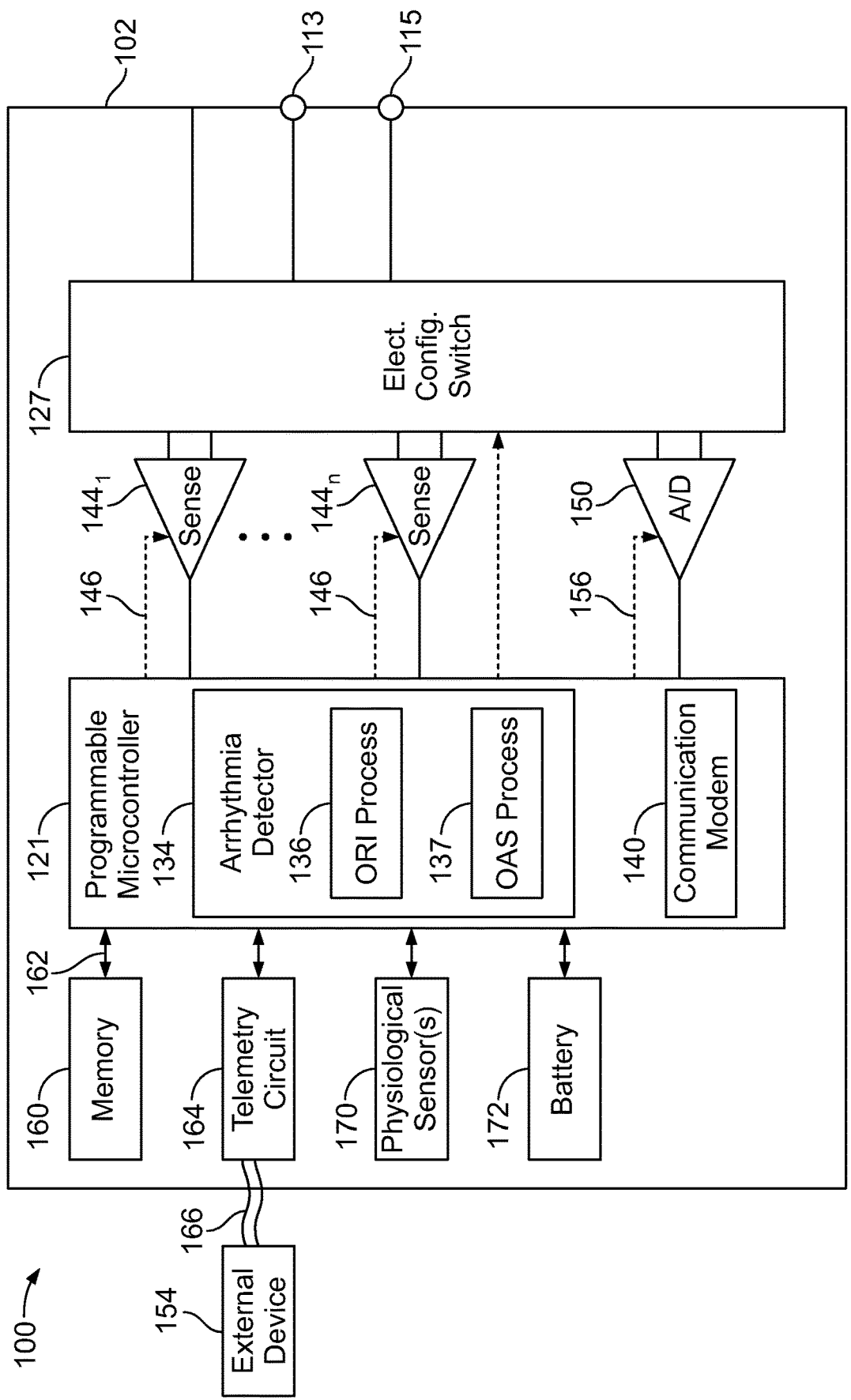
FIG. 2 illustrates a block diagram of an implantable medical device (IMD) that which is capable of treating both fast and slow arrhythmias with stimulation therapy, including cardioversion, defibrillation, and pacing stimulation in accordance with embodiments herein.

FIG. 2 shows a block diagram of the ICM 100 formed in accordance with embodiments herein. The ICM 100 may be implemented to monitor ventricular activity alone, or both ventricular and atrial activity through sensing circuit. The ICM 100 has a housing 102 to hold the electronic/computing components. The housing 102 (which is often referred to as the "can", "case", "encasing", or "case electrode") may be programmably selected to act as an electrode for certain sensing modes. Housing 102 further includes a connector (not shown) with at least one terminal 113 and optionally additional terminals 115. The terminals 113, 115 may be coupled to sensing electrodes that are provided upon or immediately adjacent the housing 102. Optionally, more than two terminals 113, 115 may be provided in order to support more than two sensing electrodes, such as for a bipolar sensing scheme that uses the housing 102 as a reference electrode. Additionally or alternatively, the terminals 113, 115 may be connected to one or more leads having one or more electrodes provided thereon, where the electrodes are located in various locations about the heart. The type and location of each electrode may vary.

The ICM 100 includes a programmable microcontroller 121 that controls various operations of the ICM 100, including cardiac monitoring. Microcontroller 121 includes a microprocessor (or equivalent control circuitry), RAM and/or ROM memory, logic and timing circuitry, state machine circuitry, and I/O circuitry. The microcontroller 121 also performs the operations described herein in connection with collecting cardiac activity data and analyzing the cardiac activity data to identify AF episodes.

A switch 127 is optionally provided to allow selection of different electrode configurations under the control of the microcontroller 121. The electrode configuration switch 127 may include multiple switches for connecting the desired electrodes to the appropriate I/O circuits, thereby facilitating electrode programmability. The switch 127 is controlled by a control signal 128 from the microcontroller 121. Optionally, the switch 127 may be omitted and the I/O circuits directly connected to the housing electrode 114 and a second electrode 126. Microcontroller 121 includes an arrhythmia detector 134 that is configured to analyze cardiac activity signals to identify potential AF episodes as well as other arrhythmias (e.g., Tachycardias, Bradycardias, Asystole, etc.). By way of example, the arrhythmia detector 134 may implement an AF detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and managing pacing therapies.

The ICM 100 is further equipped with a communication modem (modulator/demodulator) 140 to enable wireless communication. In one implementation, the communication modem 140 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 140 may be implemented in hardware as part of the microcontroller 121, or as software/firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 100 includes sensing circuit (or circuitry) 144 selectively coupled to one or more electrodes that perform sensing operations, through the switch 127 to detect cardiac activity data indicative of cardiac activity. The sensing circuit 144 may include dedicated sense amplifiers, multi-plexed amplifiers, or shared amplifiers that define multiple sensing channels, such as primary, upper guard, lower guard sensing channels. It may further employ one or more low power, precision amplifiers with programmable gain and/or automatic gain control, bandpass filtering, and threshold detection circuits to selectively sense the features of interest. In one embodiment, switch 127 may be used to determine the sensing polarity of the cardiac signal by selectively closing the appropriate switches.

Examples of the sensing circuit 144 are described herein, such as in connection with FIGS. 3-11. The output of the sensing circuit 144 is connected to the microcontroller 121 which, in turn, determines when to store the cardiac activity data of CA signals (digitized by the ND data acquisition system 150) in the memory 160. For example, the microcontroller 121 may only store the cardiac activity data (from the ND data acquisition system 150) in the memory 160 when a potential AF episode is detected. The sensing circuit 144 receives a control signal 146 from the microcontroller 121 for purposes of controlling the gain, threshold, polarization charge removal circuitry (not shown), and the timing of any blocking circuitry (not shown) coupled to the inputs of the sensing circuit. For example, the control signal 146 may cause or may include instructions/commands to change a threshold voltage for one or more of a primary detection threshold, an upper guard threshold, or a lower guard threshold.

In the example of FIG. 2, a single sensing circuit 144 is illustrated. Optionally, the ICM 100 may include multiple sensing circuitries or circuits, similar to sensing circuit 144, where each sensing circuit is coupled to two or more electrodes and controlled by the microcontroller 121 to sense electrical activity detected at the corresponding two or more electrodes. The sensing circuit 144 may operate in a unipolar sensing configuration or in a bipolar sensing configuration. Optionally, the sensing circuit 144 may be removed entirely and the microcontroller 121 perform the operations described herein based upon the CA signals from the ND data acquisition system 150 directly coupled to the electrodes.

For embodiments that include multiple sensing circuits 144 (e.g., sensing circuit 1441, ... 144*n*), each of the sensing circuits may represent a separate sensing channel in which each sensing channel may receive a control signal 146 from the microcontroller 121. The control signal 146 may cause or include instructions/commands for adjusting one or more parameters, such as threshold voltages. Different sensing channels may also include different dedicated circuitry. For example, different sensing channels may apply different filters for selectively filtering and amplifying R-waves, P-waves, and T-waves.

In other embodiments, the output from a single sensing circuit 144 is provided by the sensing circuit 144 to multiple separate sensing channels. For example, each of the sensing channels may have an independently-controlled sense amplifier or threshold comparator (not shown), such as those shown in FIG. 4. In such embodiments, the same output signal may be processed, in parallel, by multiple sensing channels. Each sensing channel may have a different threshold (e.g., a primary detection threshold, an upper guard threshold, or a lower guard threshold.)

The arrhythmia detector 134 of the microcontroller 121 includes an on-board R-R interval irregularity (ORI) process 136 that detects AF episodes using an automatic detection algorithm that monitors for irregular ventricular rhythms that are commonly known to occur during AF. The ORI process 136 may additionally or alternatively detect bradycardia, systole, pause, tachycardia episodes and the like, The ORI process 136 may be implemented as firmware, software and/or circuits. The ORI process 136 uses a hidden Markov Chains and Euclidian distance calculations of similarity to assess the transitionary behavior of one R-wave (RR) interval to another and compare the patient's RR interval transitions to the known RR interval transitions during AF and non-AF episodes obtained from the same patient and/or many patients. The ORI process 136 detects AF episodes over a short number of RR intervals. For example, the ORI process 136 may implement the AF detection methods described in U.S. Pat. No. 8,135,456, the complete subject matter of which is incorporated herein by reference in its entirety. As explained herein, the ORI process 136 manages a sensitivity profile of the sensor 144 during R-wave detection utilizing an automatic sensing control (ASC) adjustment to determine whether the CA signal has sufficient amplitude to be analyzed for cardiac events. The ORI process 136 identifies R-waves within the CA signals at points where the CA signal crosses the sensitivity profile (outside of a refractory period). The ORI process 136 tracks RR intervals within the CA signal and identifies AF events within the CA signal based on irregularities in the RR interval. When a sufficient number (e.g., X cardiac events out of Y cardiac events) of the cardiac events within the CA signal are identified as AF events, the ORI process 136 declares an AF episode.

Optionally, the microcontroller 121 may also include an on-board adaptive-sensing (OAS) process 137 configured to implement one or more of the operations discussed herein. The OAS process may be executed by the arrhythmia detector 134 and may be implemented as firmware, software and/or circuits. For example, the OAS process 137 may be used to identify one or more of R-waves, noise, P-waves, and T-waves, and/or other characters-of-interest. The OAS process 137 may include features that are similar or identical to the ORI process 136 and may operate parallel to or alternatively to the ORI process 136. For example, the OAS process 137 may manage a sensitivity profile of the sensing circuit 144 during R-wave detection utilizing an automatic sensing control (ASC) adjustment to determine whether the CA signal has sufficient amplitude to be analyzed for cardiac events. The OAS process 137 may identify R-waves within the CA signals at points where the CA signal crosses a primary detection threshold (outside of a refractory period). The OAS process 137 may track RR intervals or may communicate with the ORI process 136 for tracking the RR intervals. Optionally, the OAS process 137 may identify AF events within the CA signal based on irregularities in the RR interval in as similar manner as described above with respect to the ORI process 136.

Figure 3A:
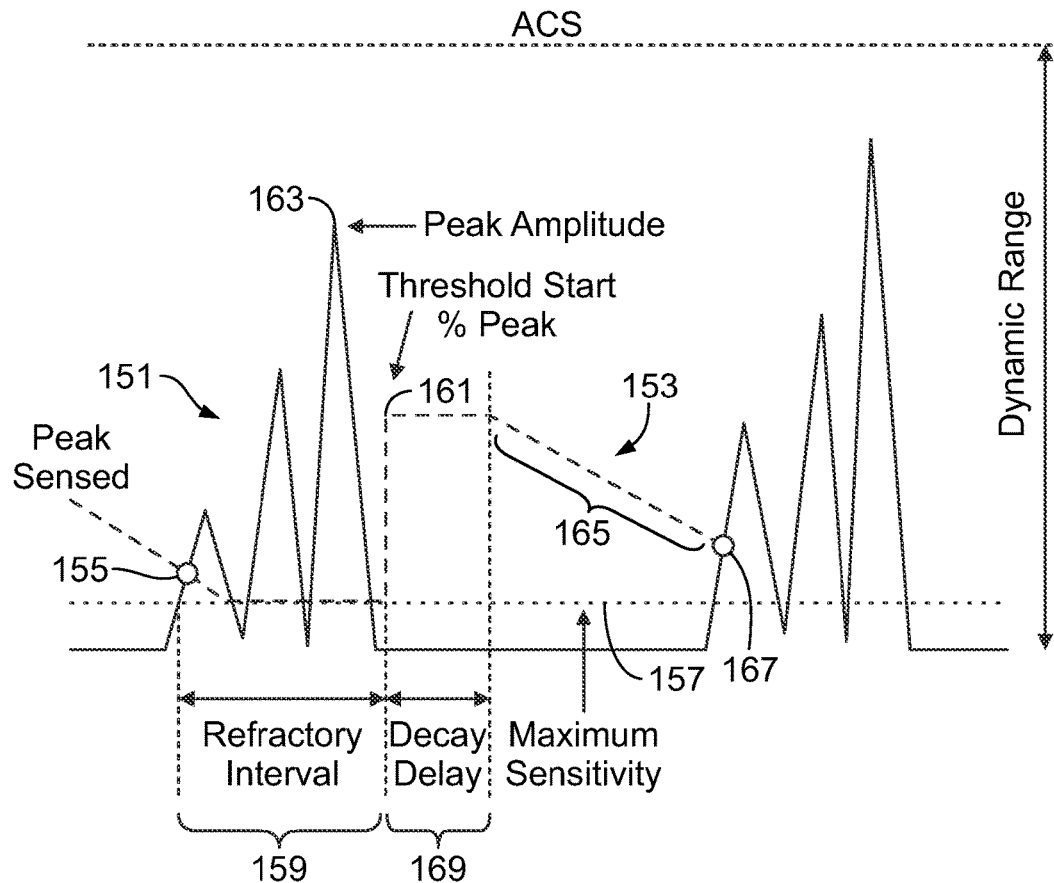
FIG. 3A illustrates an automatic sensing control (ASC) adjustment process that may be utilized by the ICM in accordance with embodiments herein.

FIG. 3A illustrates an automatic sensing control (ASC) adjustment that may be utilized by the ORI process 136 of the ICM 100 in accordance with embodiments herein. FIG. 3A illustrates an example cardiac activity signal 151, in connection with a single sensing channel, after passing through a rectifier to convert all positive and negative deflections within the cardiac activity signal 151 to be positive deflections. The ORI process 136 manages the sensing circuit 144 to have a sensitivity profile 153 (denoted by a dashed line) that varies over time for the one (e.g., primary) sensing channel.

In a basic implementation, the ORI process 136 utilizes a conventional ASC adjustment based on a conventional sensitivity profile 153. The sensitivity profile 153 is defined by sensitivity profile parameter settings corresponding to the threshold start sensitivity 161, decay delay parameter 169, maximum sensitivity 157 and slope of the sensitivity decay 165. Optionally, the sensitivity decay 165 may be flat (e.g., horizontal) or defined in accordance with a non-linear monotonically changing shape from the threshold start sensitivity 161 to the maximum sensitivity 157. The start sensitivity parameter defines a start sensitivity of the sensitivity profile. For example, the start sensitivity parameter may set start sensitivity to a percentage of the preceding R-wave amplitude. The refractory period/interval duration parameter defines a blanking interval beginning at a sensed R-wave, during which the processors do not search for a T-wave. The decay delay parameter defines the interval at which the sensitivity profile maintains the sensitivity level at a constant level following expiration of the refractory period before the sensitivity profile begins decreasing. When the sensitivity profile includes a linear sensitivity level decline, the decay delay rate defines a slope of the linear sensitivity level decline. The maximum sensitivity limit defines a lowest sensitivity level (e.g., maximum resolution) that linear sensitivity decline is allowed to reach. The sensitivity parameters are preprogrammed to fixed values and, over the operation of the implantable medical device (IMD), are only modified (if at all) by a clinician.

In accordance with the sensitivity profile 153, when the CA signal 151 crosses the sensitivity profile 153 at starting point 155, the ORI process 136 treats the point 155 as a sensed R-wave and begins a refractory interval 159. No new R-wave (or T-wave) will be sensed during the refractory interval 159. At the end of the refractory interval 159, the sensitivity is adjusted to a threshold start sensitivity 161. The threshold start sensitivity 161 is defined as a percentage of the amplitude 163 of the QRS complex of the CA signal 151 detected during the refractory interval 159. The sensing circuit 144 maintains the threshold start sensitivity 161 for a decay delay parameter 169, after which the ORI process 136 begins to monotonically decrease the sensitivity (increase the resolution) of the sensing circuit 144 as denoted by the sensitivity decay 165 within the sensitivity profile 153. The sensing circuit 144 continues to decrease the sensitivity until either the sensitivity decay 165 reaches the maximum sensitivity 157 or an amplitude of the rectified cardiac activity signal 151 exceeds the sensor sensitivity profile 153, such as at a point 167 where a new sensed R-wave is detected. Optionally, the sensitivity profile 153 may remain constant over an entire cardiac cycle (e.g., from start point 155 to point 161 or to point 167).

The sensitivity of the sensing circuit 144 (FIG. 2) is continuously adjusted (or held constant) by the microcontroller 121 in accordance with the sensitivity profile 153 over the course of an individual cardiac event.

Next, the discussion turns to examples that utilize multiple sensing channels that operate in parallel to analyze common CA signals. In the following examples, the sensitivity profile over at least the R-wave portion of the CA signals is maintained constant for each individual beat. The sensitivity profile has corresponding detection thresholds that are assigned to each sending channel for a particular beat (and event prediction window). The detection threshold is adjusted to change the sensitivity for the corresponding sending channel and for the corresponding subsequent beat.

Figure 3B:
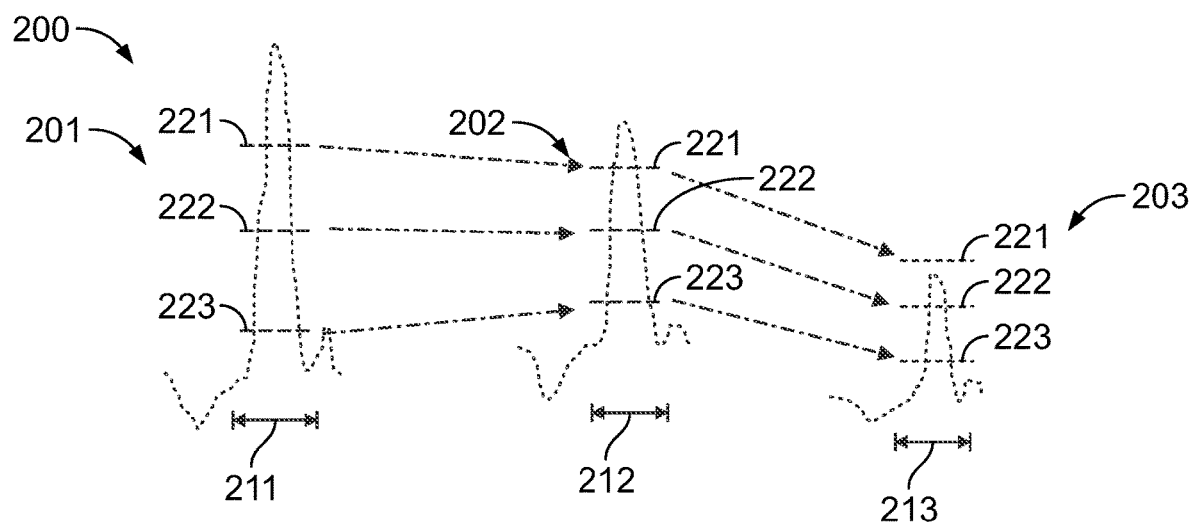
FIG. 3B illustrates another ASC adjustment that may be utilized by the ICM in accordance with embodiments herein.

FIG. 3B illustrates another ASC adjustment that may be utilized by the OAS process 137 of the ICM 100 in accordance with embodiments herein. The ASC adjustment of the OAS process 137 may be executed in parallel with, or alternatively to, the ASC adjustment of the ORI process 136.

As shown, FIG. 3B illustrates cardiac activity signals 200 that include three beats 201, 202, 203. In a basic implementation, the OAS process 137 determines an event prediction window for each beat (also referred to as a beat-of-interest) and then observes whether the CA signals exceed two or more thresholds for multiple sensing channels during the event prediction window. For example, the OAS process 137 may determine event prediction windows 211, 212, 213 for the beats 201, 202, 203, respectively. An event prediction window represents a time period in which the CA signals are observed to determine whether the CA signals exceed one or more of the thresholds. An event prediction window may be determined prior to the associated beat in real-time. For example, the OAS process 137 may use data observed in the event prediction window 211 at beat 201 for determining a timing and duration of the event prediction window 212 of the subsequent beat 202 and the timing and duration of the event prediction window 213 of the next beat 203. The OAS process 137 may use the data determined at beat 202 for determining a timing and duration of the event prediction window 213 for the subsequent beat 203 and so on. Alternatively, the event prediction windows 211-213 may be determined and applied to a cardiac activity data set that includes historical data.

For some embodiments, the ASC adjustment of the OAS process 137 may operate without conventional (or preset) refractory periods/intervals or blanking intervals. Instead, the time period for identifying the R-wave is defined by the event prediction window. Upon detecting the R-wave, the subsequent event prediction window is calculated based on a number of parameters, such as prior amplitudes, morphology of the R-wave, noise floor, and event intervals, such as P-P, P-R, R-T, and R-R intervals over time. In some embodiments, the thresholds are not subject to sensitivity decay. Instead, the threshold may be constant throughout the event prediction window as indicated in FIG. 3B. In other embodiments, a sensitivity decay (threshold increase) or a sensitivity enhancement (threshold decrease) may occur over time through the event prediction window.

In addition to determining the event prediction window for the next beat, the OAS process 137 decides whether to adjust (e.g., increase or decrease) the two or more thresholds for the next beat and, if so, how much to adjust the thresholds. In the illustrated embodiment, the thresholds include a primary detection threshold 222, an upper guard threshold 221, and a lower guard threshold 223. The upper guard threshold 221 is greater than the primary detection threshold 222 and greater than the lower guard threshold 223. The lower guard threshold 223 is less than the primary detection threshold 222 such that the primary detection threshold 222 is positioned between the upper guard threshold 221 and the lower guard threshold 223. The upper and lower guard thresholds 221, 223 are offset from the primary detection threshold 222 and may be used to determine whether to change the primary detection threshold 222 or allow the primary detection threshold 222 to remain the same.

Although FIG. 3B illustrates three thresholds being applied to the CA signals 200 for each beat, it should be understood that only two thresholds or more than three thresholds may be applied to at least some of the beats.

In some embodiments, the primary detection threshold 222 is set about halfway between the upper and lower guard thresholds 221, 223. The three thresholds may be approximately evenly distributed. For example, the lower guard threshold 223 may be set at 25% of the difference between the amplitude and the noise floor of the prior beat, the primary detection threshold 222 may be set at 50% of the difference between the amplitude and the noise floor of the prior beat, and the upper guard threshold 221 may be set at 75% of the difference between the amplitude and the noise floor of the prior beat. In some embodiments, the thresholds are set at approximately the above values (e.g., between +1-10% of the value). For example, approximately 25% means a value between 15-35%, approximately 50% means a value between 40-60%, and approximately 75% means a value between 65-85%. In other embodiments, however, the thresholds may be distributed more unevenly (e.g., 10%, 65%, 90% of the difference between the amplitude and the noise floor of the prior beat).

Optionally, the lower guard threshold may be set at the noise floor or below the noise floor. Alternatively, an additional threshold (e.g., a fourth threshold) may be set at the noise floor or below the noise floor. Such thresholds may be used to identify the noise floor or monitor the noise floor.

For embodiments that may only utilize two thresholds (e.g., a primary detection threshold and a guard threshold), the primary detection threshold and guard threshold may be set closer to the noise floor. For example, the two thresholds may be set at 15% and 45% of the difference between the amplitude and the noise floor of the prior beat. Alternatively, the two thresholds may be separated further from each other. For example, the two thresholds may be set at 20% and 75% of the difference between the amplitude and the noise floor of the prior beat.

After determining the event prediction window and whether and how to adjust the thresholds for a beat, the OAS process 137 then observes whether the CA signals 200 within the event prediction window exceed one or more of the thresholds. When the CA signals 200 exceed one or more of the thresholds, this data may be utilized for determining how to adjust the sensing channel thresholds for the subsequent beat.

In some embodiments, the guard thresholds operate as flags or triggers that automatically cause the thresholds to increase or decrease for the next beat. Embodiments may effectively count the number of times that the CA signals exceed the thresholds within the event prediction window to determine whether and how to change the thresholds. For example, if an upper guard threshold is exceeded for a select number of beats, one or more processors may automatically increase some or all of the sending channel thresholds in a predetermined manner. If the primary detection threshold is exceeded but not the upper guard threshold for a select number of beats, the one or more processors may automatically change some or all of the sensing channel thresholds in a predetermined manner or decide to not change the thresholds. If a lower guard threshold is exceeded but not the primary detection threshold for a select number of beats, the one or more processors may automatically decrease some or all of the sending channel thresholds in a predetermined manner. A change in a "predetermined manner" may include changing the thresholds by a fixed amount (e.g., 20% increase of current threshold) or may include changing the thresholds based on a function (e.g., 20% increase of the difference between the amplitude and the noise floor).

Figure 4:
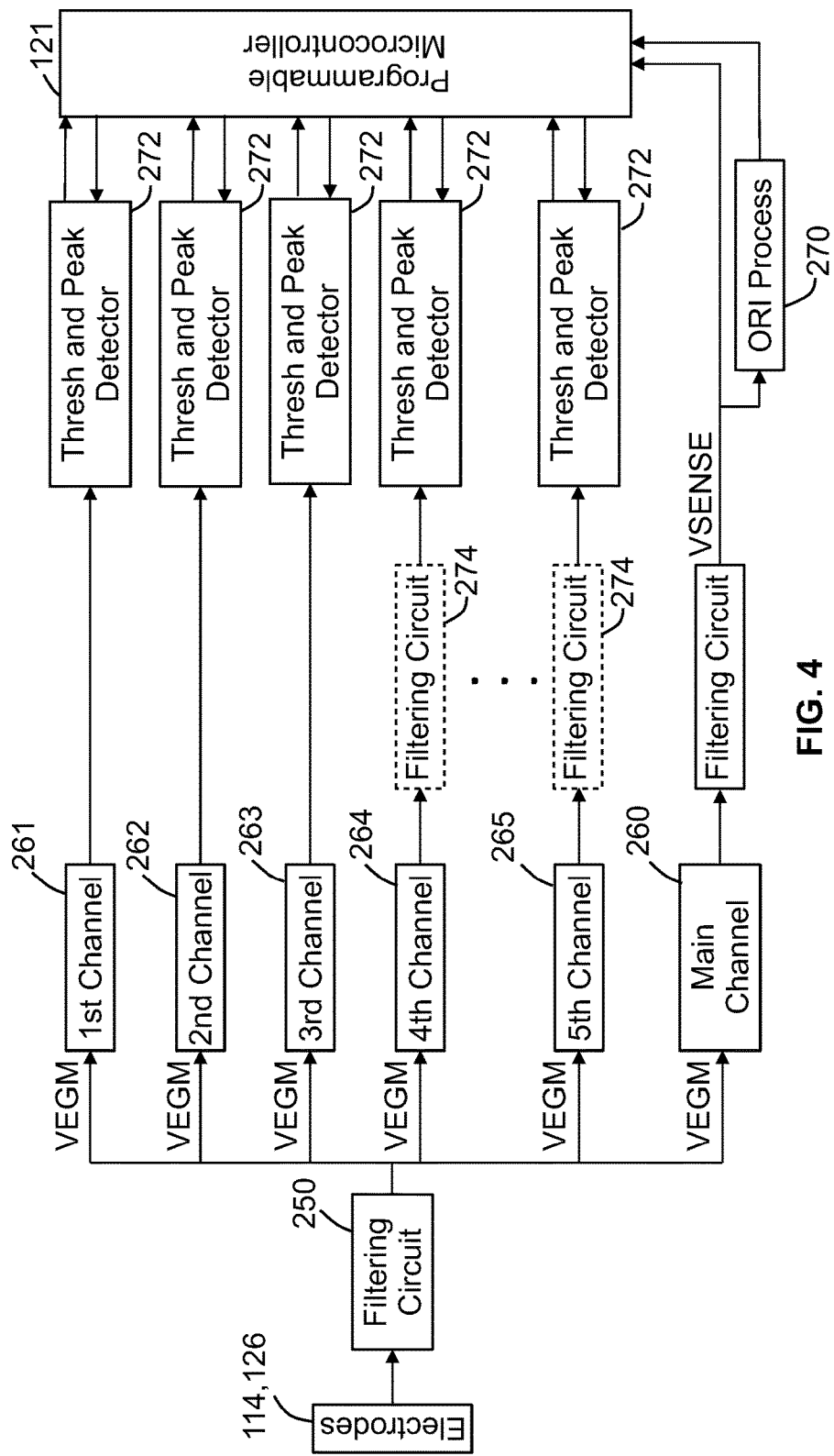
FIG. 4 illustrates a block diagram of parallel signal processing implemented in accordance with embodiments herein.

FIG. 4 illustrates a block diagram of parallel signal processing paths implemented in accordance with embodiments herein. The electrodes 114, 126 collect CA signals for a series of cardiac events or beats. The ICM 100 (FIG. 1) may perform sensing using a wide frequency bandpass filtering circuit 250 to collect EGM (or VEGM) signal that contains P, QRS, and/or T-waves. The VEGM signal may be processed along a main sensing channel 260 and one or more other sensing channels. In the illustrated embodiment, the other sensing channels include a first sensing channel 261, a second sensing channel 262, a third sensing channel 263, and a fourth sensing channel 264. FIG. 4 also shows an $n^{th}$ sensing channel 265 that indicates embodiments may have more than four sensing channels. For example, in some embodiments, the IMD 100 may include 16 total channels, including the main sensing channel 260.

In the main sensing channel 260, sensed cardiac activity signals (e.g., VEGM signals) are passed through a hardware filtering circuit 266 to form a filtered cardiac activity (VSENSE) signal. The VSENSE signal may be analyzed by an onboard arrhythmia detection process within the ICM for AD, brady, systole, pause and/or tachy episodes and the like.

In some embodiments, the same VEGM signal is processed in one or more of the other sensing channels 261-265. In some embodiments, each of the sensing channels 261-265 includes threshold and peak amplitude detector 272. The detectors 272 may include, for example, a threshold comparator having an adjustable voltage detection threshold value for comparing to the CA signals. The reference voltage detection threshold may be adjusted by, for example, the microcontroller 121 or other circuitry. Optionally, one or more of the sensing channels 261-265 may include a filtering circuit.

In particular embodiments, the ASC adjustment utilizes multiple sensing channels to determine whether to adjust one or more of the thresholds that are applied to the CA signals within an event prediction window. For example, the detector 272 of the first sensing channel 261 may apply a primary detection threshold to the VEGM signals, the detector 272 of the second sensing channel 262 may apply an upper guard threshold to the VEGM signals, the detector 272 of the third sensing channel 263 may apply a lower guard threshold to the VEGM signals. Optionally, one or more of the detectors 272 of the sensing channels 264, 265 may apply a different threshold to the VEGM signals within the event prediction window.

Such parallel processing may facilitate identifying sensed events (e.g., P-waves, T-waves, R-waves) in the event prediction windows and modifying the thresholds applied to the CA signals of the different beats. For example, each of the detectors 272 of the sensing channels 261-265 provides an output, when the CA signals exceed the corresponding threshold. For embodiments that utilize multiple sensing channels, the microcontroller may count the number of outputs received to determine how to adjust, if at all, the thresholds (e.g., reference voltages) of the detectors 272. Alternatively, the microcontroller may determine how to adjust, if at all, the thresholds based on which of the responsive sensing channels has the highest threshold.

In other embodiments, however, the sensing channels 264, 265 may be used to distinguish R-waves and P-waves, distinguish R-waves and T-waves, or distinguish other sensed events (e.g., within the same beat). For example, the sensing channel 264 may include a filtering circuit 274 (e.g., pass band) that is set around an R-wave dominant frequency and the sensing channel 265 may include a filtering circuit 274 (e.g., pass band) that is set around a P-wave dominant frequency. Because their dominant frequencies are not the same, the sensing channel 264 may amplify the R-wave more than the P-wave while the sensing channel 265 may amplify the P-wave more than the R-wave. As described herein, such parallel processing may facilitate identifying P-waves in the event prediction windows. Alternatively, the sensing channel 264 may include a filtering circuit 274 (e.g., pass band) that is set around an R-wave dominant frequency and the sensing channel 265 may include a filtering circuit 274 (e.g., pass band) that is set around a T-wave dominant frequency.

In some embodiments, one or more of the sensing channels may be used to monitor a noise floor. For example, the sensing channel 264 may be filtered to provide VSENSE signals and a threshold may be selected so that noise between certain events may be detected. For example, a noise floor may be identified by measuring segments of CA signals that occur during intervals between two adjacent sensed events (e.g., during a refractory period). Alternatively or in addition to this, one of the sensing channels may have a threshold set below the noise floor to detect and measure noise amplitudes.

Returning to FIG. 2A, the ICM 100 further includes an analog-to-digital A/D data acquisition system (DAS) 150 coupled to one or more electrodes via the switch 127 to sample cardiac activity signals across any pair of desired electrodes. The data acquisition system 150 is configured to acquire cardiac electrogram (EGM) signals as CA signals, convert the raw analog data into digital data, and store the digital data as CA data for later processing and/or telemetric transmission to an external device 154 (e.g., a programmer, local transceiver, or a diagnostic system analyzer). The data acquisition system 150 is controlled by a control signal 156 from the microcontroller 121.

By way of example, the external device 154 may represent a bedside monitor installed in a patient's home and utilized to communicate with the ICM 100 while the patient is at home, in bed or asleep. The external device 154 may be a programmer used in the clinic to interrogate the ICM 100, retrieve data and program detection criteria and other features. The external device 154 may be a handheld device (e.g., smartphone, tablet device, laptop computer, smartwatch, and the like) that can be coupled over a network (e.g., the Internet) to a remote monitoring service, medical network and the like. The external device 154 facilitates access by physicians to patient data as well as permitting the physician to review real-time CA signals while collected by the ICM 100.

The microcontroller 121 is coupled to a memory 160 by a suitable data/address bus 162. The programmable operating parameters used by the microcontroller 121 are stored in memory 160 and used to customize the operation of the ICM 100 to suit the needs of a particular patient. Such operating parameters define, for example, detection rate thresholds, sensitivity, automatic features, AF detection criteria, activity sensing or other physiological sensors, and electrode polarity, etc.

In addition, the memory 160 stores the cardiac activity data, as well as the markers and other data content associated with detection of arrhythmia episodes. The operating parameters of the ICM 100 may be non-invasively programmed into the memory 160 through a telemetry circuit 164 in telemetric communication via communication link 166 with the external device 154. The telemetry circuit 164 allows intracardiac electrograms and status information relating to the operation of the ICM 100 (as contained in the microcontroller 121 or memory 160) to be sent to the external device 154 through the established communication link 166. In accordance with embodiments herein, the telemetry circuit 164 conveys the cardiac activity data, markers and other information related to AF episodes.

The ICM 100 may further include magnet detection circuitry (not shown), coupled to the microcontroller 121, to detect when a magnet is placed over the unit. A magnet may be used by a clinician to perform various test functions of the housing 102 and/or to signal the microcontroller 121 that the external device 154 is in place to receive or transmit data to the microcontroller 121 through the telemetry circuits 164.

The ICM 100 can further include one or more physiologic sensors 170. Such sensors are commonly referred to (in the pacemaker arts) as "rate-responsive" or "exercise" sensors. The physiological sensor 170 may further be used to detect changes in the physiological condition of the heart, or diurnal changes in activity (e.g., detecting sleep and wake states). Signals generated by the physiological sensors 170 are passed to the microcontroller 121 for analysis and optional storage in the memory 160 in connection with the cardiac activity data, markers, episode information and the like. While shown as being included within the housing 102, the physiologic sensor(s) 170 may be external to the housing 102, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 172 provides operating power to all of the components in the ICM 100. The battery 172 is capable of operating at low current drains for long periods of time. The battery 172 also desirably has a predictable discharge characteristic so that elective replacement time can be detected. As one example, the housing 102 employs lithium/silver vanadium oxide batteries. The battery 172 may afford various periods of longevity (e.g., three years or more of device monitoring). In alternate embodiments, the battery 172 could be rechargeable. See for example, U.S. Pat. No. 7,294,108, Cardiac event micro-recorder and method for implanting same, which is hereby incorporated by reference. also reduce implant time and introduce less change in body image for patients.

Figure 5:
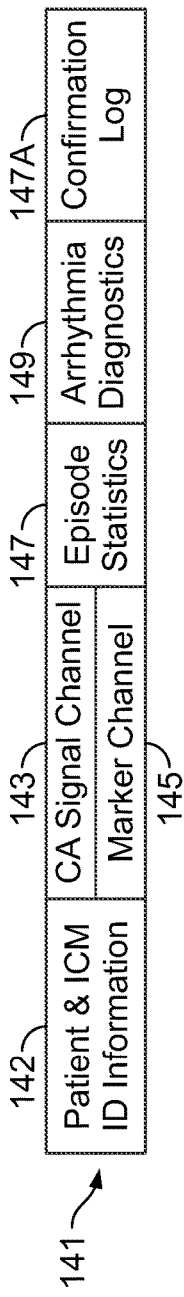
FIG. 5 illustrates cardiac activity data generated and stored by an ICM in accordance with embodiments herein.

FIG. 5 illustrates cardiac activity data generated and stored by the ICM 100 in memory 160 in accordance with embodiments herein. The CA data set 141 is stored by the ICM in response to detection of episodes of interest, patient initiated instructions, physician initiated instructions and the like. The CA data set 141 may include, among other things, patient and ICM identification information 142. By way of example, the patient identification information may include a patient unique medical record number or other identifier, patient name and/or patient demographic information. The ICM ID may include a serial number or other unique identifier of the ICM, software and firmware version numbers, and/or a unique wireless ID. The CA data set 141 includes one or more signal channels 143 that store CA signals collected by a corresponding sensing channel (e.g., sensor circuit 144 or DAS 150). The CA signal channel 143 may include EGM signals for a series of cardiac beats/events sensed by the ICM. The CA data set 141 also includes a marker channel 145 having, among other things, device documented markers identified by the ICM 100 in connection with the CA signal. The device documented markers within the marker channel 145 may include device documented markers indicative of normal sinus features, AF detected events, AF detected episodes and the like. For example, the ORI process 136 (FIG. 2) utilizes the sensitivity profile 153 (FIG. 3A) or the OAS process 137 to identify R-waves in the CA signal.

The CA data set 141 also includes episode statistics 147 and arrhythmia diagnostics 149. The episode statistics 147 may be presented in a window on a user interface to list various statistical data for any or all episodes recorded by the ICM 100 since the episode and CA data storage were last cleared. Optionally, the episode statistics 147 may also list the number of inhibited VT diagnoses due to arrhythmia qualifiers, such as a bigeminal rhythm qualifier, and/or other rhythm discriminators. As further non-limiting examples, the episode statistics 147 may also include a date of a last programmer session, date of the last ICM interrogation, the date of the presently stored episodes and the date when EGMs were last cleared from the ICM and the like.

Optionally, the CA data set 141 may also include a confirmation log 147A that may be calculated in real-time or off-line in accordance with embodiments herein. For example, the original CA data set 141 may be generated by the ICM based on the ORI process or the OAS process described herein. The CA data set 141 is telemetered from the ICM to a local external device and/or remote server.

Figure 6:
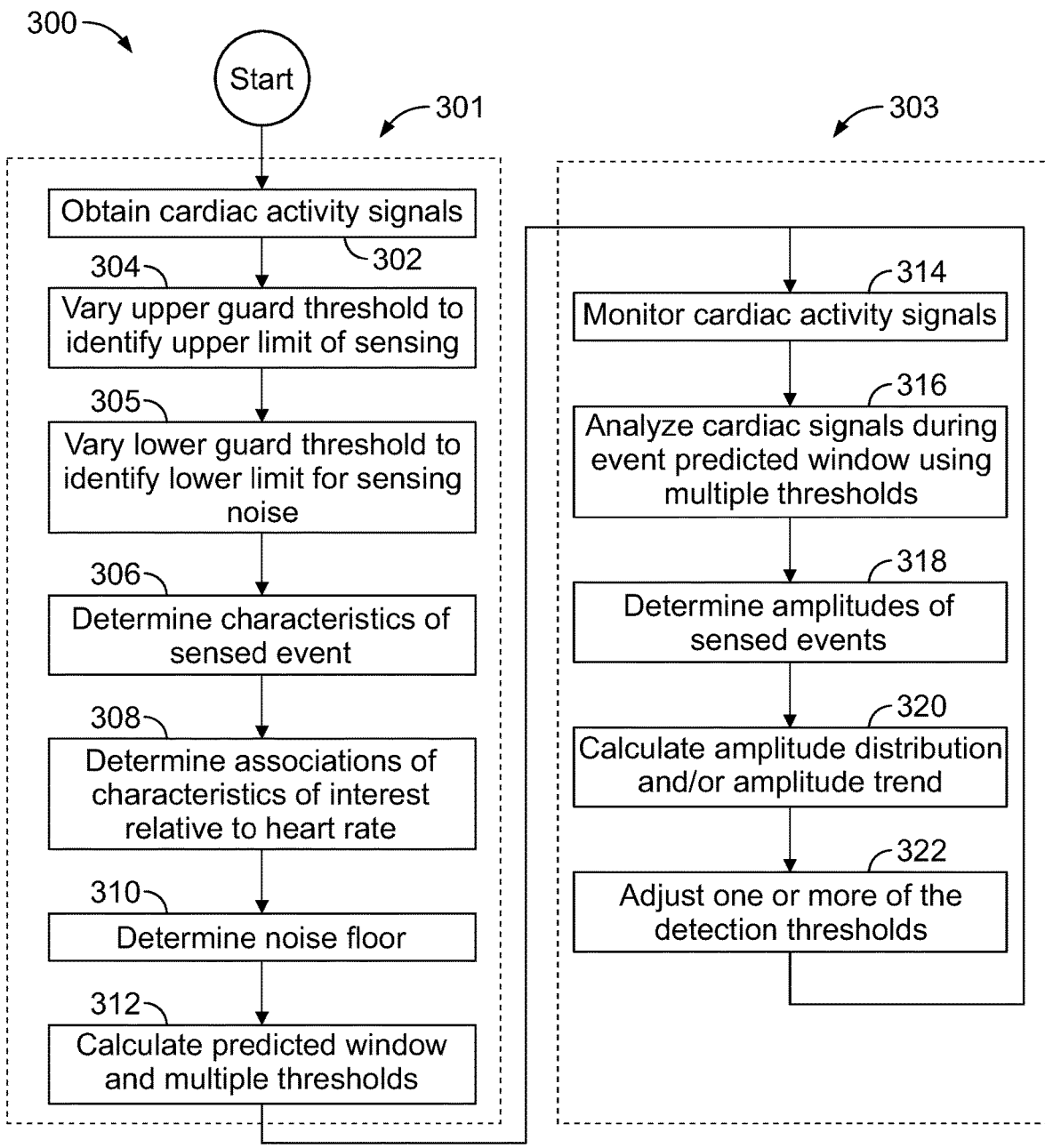
FIG. 6 illustrates a flow chart for determining different parameters and thresholds that may be used to modify an adaptive-sensing process implemented in accordance with embodiments herein that includes.

FIG. 6 illustrates an adaptive-sensing process 300 that may be used to determine an event prediction window and thresholds, such as an ASC process. As shown, the process 300 includes an initialization stage or sub-process 301, in which CA signal data is analyzed to determine how to calculate event prediction windows and corresponding thresholds, including a first event prediction window and corresponding thresholds. For example, data may be collected for generating a function for calculating future event prediction windows and a function for calculating future thresholds. The process 300 may also include a device-operation stage or sub-process 303 in which CA signal data is obtained and analyzed in real-time.

The initialization stage 300 analyzes historical CA signal data or real-time CA signal data to determine how to calculate event prediction windows and corresponding thresholds during the device-operation stage 303. A function for calculating future event prediction windows may be based on an R-R interval distribution and/or an R-R interval trend. A function for calculating thresholds for the event prediction windows may be based on at least one of a peak amplitude distribution of R-waves, a peak amplitude trend of R-waves, a noise floor distribution, or a noise floor trend. For processes used to detect P-waves or T-waves, the same parameters for the respective sensed events may be used to calculate the function. However, the initial event prediction window and thresholds may be determined by identifying the R-wave in one sensing channel and then searching a window in another sensing channel that occurs prior to or after the sensed R-wave (e.g., 500 milliseconds prior to the R-wave or 200-700 milliseconds after the R-wave).

At 302, one or more processors of the system obtain CA signals (e.g., ECG signals, EGM signals, VSENSE signals, or VEGM signals) corresponding to a series of beats. The CA signals may be obtained in real-time or previously acquired and stored in memory of an implantable or external monitoring device, implantable or external therapy delivery device, programmer, workstation, healthcare network or other system. When the CA signals were previously acquired, the obtaining operation at 302 represents accessing and reading the previously stored cardiac activity data.

The CA signals may be included in a CA data set in which the CA signals were recorded in connection with a series of beats. The CA data set may include a data set for detecting R-waves and, optionally, a separate data set for detecting P-waves or T-waves. In such instances, the separate data sets may be further filtered and selectively amplified for identifying the P-waves or T-waves. The CA data set may include separate data sets for multiple sensing channels as described herein.

In particular embodiments, the CA signals are acquired in real-time by an individual having an IMD, such as an ICM or an S-ICD. As the CA signals are acquired, the initialization process 301 may analyze the CA signals over one or multiple sensing channels to determine an event prediction window and thresholds.

At 304 and 305, one or more processors of the system analyze the CA signals to determine upper and lower sensing limits. For example, at 304, the CA signals may be analyzed to identify an upper limit that will, for example, likely not be exceeded by the CA signals. The CA signals may be scanned or reviewed over an extended period of time (e.g., minutes or hours) to identify a limit that was not exceeded or that was rarely exceeded. The upper sensing limit may represent a limit that the upper guard threshold will not exceed. At 305, a lower sensing limit may be raised or lower to identify a threshold at which noise can be monitored and/or a noise floor. The CA signals may be scanned or reviewed over an extended period of time (e.g., minutes or hours) to identify a lower limit that the peak of the sensed event generally exceeded or was never below. The lower sensing limit may represent a minimum sensing level that is the lowest threshold that will be used for monitoring for peaks in the sensed events.

At 306, one or more processors of the system analyze the CA signals for one or more characteristics of interest. For example, the characteristic of interest may be a peak in R-waves, T-waves, P-waves, slew rates for the sensed events in the series of beats, morphologies of the sensed events for the series of beats, a noise floor between sensed events, and one or more event intervals (e.g., P-P, P-R, R-T, and R-R intervals). At 308, one or more processors of the system determine associations between the heart rate and one or more characteristics of interest.

At 310, one or more processors of the system determine a noise floor. The noise floor may be calculated by analyzing the CA signals between two sensed events (e.g., R-waves) for peaks in the noise present within the CA signals. For example, a noise floor may be identified by measuring multiple CA signal data samples between two adjacent sensed events. Alternatively or in addition, one of the sensing channels may have a threshold set below the noise floor to detect and measure noise amplitudes, such as between an end of a T-wave and beginning of the next P-wave.

Noise parameters that may be used to estimate a noise level or a noise floor include an absolute peak, a mean of absolute values, a median of absolute values, a mode of absolute values (such as a most likely absolute value which may be found as the peak of a probability density estimate), a root-mean square, and a mean square over the series of collected electrogram samples. The noise parameter may also be computed as a moving average, an autoregressive average, or a cascade or linear combination of such previously computed noise parameters or averages of such previously computed noise parameters.

Additionally or alternatively, the noise floor may be determined, at 310, by utilizing a channel with the threshold set below a noise floor to detect and measure the noise amplitude peaks over a period of time.

At 312, one or more processors of the system may calculate an event prediction window at which a designated sensed event (e.g., R-wave) will occur in the next beat. The event prediction window may be a function of the R-R intervals. In particular embodiments, the event prediction window is determined using at least one of an R-R interval distribution or an R-R interval trend. One or more processors of the system may also calculate thresholds to be applied to the CA signals within the event prediction window. The thresholds may include a primary detection threshold and one or more guard thresholds.

At 303, a real-time ASC adjustment process is initiated using, as base or initial setting, the event prediction window and the multiple thresholds determined at 312. At 314, one or more processors and/or sensing circuits monitor CA signals, for a series of beats, where different sensing channels 260-265 use of different detection thresholds. Each of the sensing channels may have a single detection threshold. For example, a first sensing channel (e.g., 260 or 261) may have a primary detection threshold, and a second sensing channel (e.g., 262) may have an upper guard threshold. Similarly, a third sensing channel (e.g., 263) is assigned a lower guard threshold, such as based on the determination at 312 and/or based on peak amplitudes for prior beats. For example, the primary detection threshold may be set closer to a midpoint between the peak amplitude of the last sensed event and a noise floor. For example, the primary detection threshold may be set at 50% of the difference between the noise floor and the peak amplitude of the previous sensed event. Optionally, the upper and lower guard thresholds may be set to 75% and 25%, respectively, of the difference between the sensed event peak amplitude and the noise floor. Optionally, the peak amplitude of the sensed event and noise floor may be based on a single beat or averaged over multiple beats.

Optionally, the detection thresholds may include a lower-limit threshold that is configured to be set at the noise floor or below the noise floor and essentially capture raw CA signals. The CA signals over the channel with the lower-limit threshold may be used for analyzing a morphology of the sensed events within the event prediction window, such as when the other channels do not detect a sensed event.

At 318, the one or more processors analyze CA signals collected over the sensing channels to determine a peak amplitude of a sensed event. The processors may determine an absolute peak of the sensed event or alternatively simply record/bin a count of whether and which sensing channels detected an event that exceeded the corresponding threshold. For example, a sensed event may be counted when exceeding one or more of the detection thresholds within the event prediction window. For some embodiments, in addition to determining simply that the CA signals have exceeded a corresponding detection threshold (and for which sensing channel), the sensing circuit (e.g., threshold-and-peak detector) may also determine a peak amplitude of the CA signals.

The processors and/or sensing circuits may maintain various counts indicative of distributions and/or trends. The processors and/or sensing circuit may count a number of beats (e.g., successive or X out of Y) for a given sensing channel detected sensed events that exceeded the corresponding threshold. For example, the count may indicate that during the last 10 beats, the lower guard channel detected 10 events, the primary channel detected 5 events, and the upper guard channel detected 3, thereby suggesting to lower thresholds. As another example, a count may indicate that for beats #1 to #4, all three channels detected events. But for beats #5 to #7, only the lower guard and primary channels detected events, thereby suggesting a downward trend.

Optionally, the raw peak amplitude to each sensed event may be recorded

At 320, the one or more processors may calculate at least one of an amplitude distribution or an amplitude trend. In some embodiments, the amplitude distribution is calculated by the microcontroller. After acquiring a plurality of data points (amplitudes), an amplitude distribution may be calculated. In some embodiments, a model distribution may be used by the microcontroller when initially acquiring data or early on in the real-time ASC adjustment process 303. For example, the model distribution may include data points (e.g., amplitudes) that represent theoretical or historic values, not actual amplitudes detected by an IMD. Instead, the model distribution may be used for adjusting future thresholds.

For example, distributions and/or trends may indicate changes in the electrode to tissue (ET) contact interface. For example as scan tissue or poor contact may cause the ET interface to reduce or dull all CA signals. The IMD may shift in the pocket to create a stronger or weaker CA signal. At certain times in a day) e.g., while asleep) the ET interface may become better or worse as compared to during the day when the patient is active or not laying down.

In a similar manner, recently acquired data points (e.g., amplitude) may be monitored over time to generate a trendline of the amplitudes. The trendline may indicate whether the amplitudes are increasing or decreasing. The trendline may include the amplitudes from at least the last two beats, the amplitudes from at least the last three beats, the amplitudes from at least the last five beats, the amplitudes from at least the last ten beats, or the amplitudes from at least the last twenty beats.

At 322, the one or more processors may adjust one or more of the detection thresholds. The detection thresholds may be increased or may be decreased or remain unchanged based on the distribution or trend. For example, if the upper guard threshold is exceeded for a select number of beats, then it is either known (based on the other sensing channels) or assumed that the detection thresholds with lower values have been exceeded. The one or more processors may increase the detection thresholds by a fixed amount (e.g., 50% of the current threshold value) based on which detection thresholds were exceeded. The amount of increase may also be a function of the amplitude of the recently sensed event (or recently sensed events). The greater the amplitude of the recent sensed event, the greater the increase to the detection threshold of the subsequent beat. More examples are described herein with respect to FIGS. 7, 8, 9, and 10.

Figure 7:
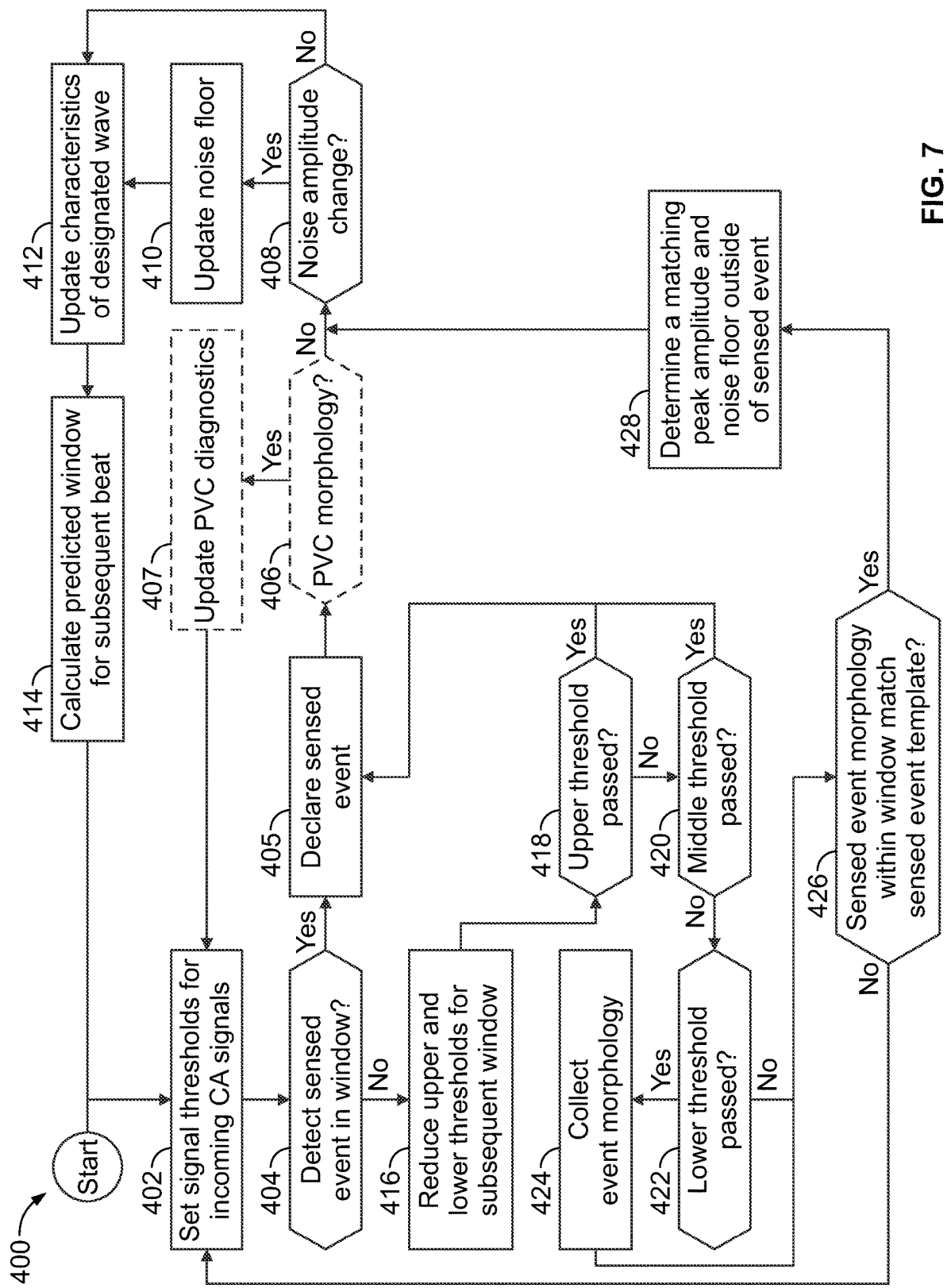
FIG. 7 is a block diagram illustrating an adaptive-sensing process for detecting R-waves that may be implemented in accordance with embodiments described herein.

FIG. 7 is a block diagram illustrating an adaptive-sensing process 400 for detecting sensed events. In the illustrated embodiment, the sensed event is an R-wave and the thresholds include a primary detection threshold, an upper guard threshold, and a lower guard threshold. It should be understood, however, the adaptive-sensing process may be used to detect sensed events other than the R-wave, such as P-waves or T-waves, and may include less than three thresholds or more than three thresholds.

At 402, one or more processors of the system may set two or more thresholds for being applied during the event prediction window. At the onset of the adaptive-sensing process 400, the event prediction window and the two or more thresholds may be provided by the initialization process 300 (FIG. 6). For example, the lower guard threshold may be set just above a noise floor to detect an increase in the noise floor. The designated point for the primary detection threshold may be set between a noise metric and an amplitude metric. The noise metric may be a noise floor or current noise level experienced by the system. For example, the primary detection threshold may be set at a midpoint (or 50%) between the noise floor and an average peak amplitude of sensed events as calculated by the initialization process 300. As another example, the primary detection threshold may also be set at a designated point between the noise floor and the expected amplitude based on the most recent CA signals as calculated by the initialization process 300.

In some embodiments, the designated point for the primary detection threshold may be set between 25%-75% of the difference between the noise metric and the amplitude metric. In certain embodiments, the designated point for the primary detection threshold may be set between 35%-65% of the difference between the noise metric and the amplitude metric. In particular embodiments, the designated point for the primary detection threshold may be set between 45%-55% of the difference between the noise metric and the amplitude metric.

At the onset of the process 400, the upper guard threshold may be set at or above the average amplitude of the CA signals analyzed during the process 300 or may be set at or above the expected amplitude based on the most recent CA signals. If positioned above the amplitude, the margin between the upper guard threshold and the amplitude may be a function of the signal-to-noise ratio. For example, the greater the S/N ration, the greater the margin between the upper guard threshold and the amplitude.

Figure 8:
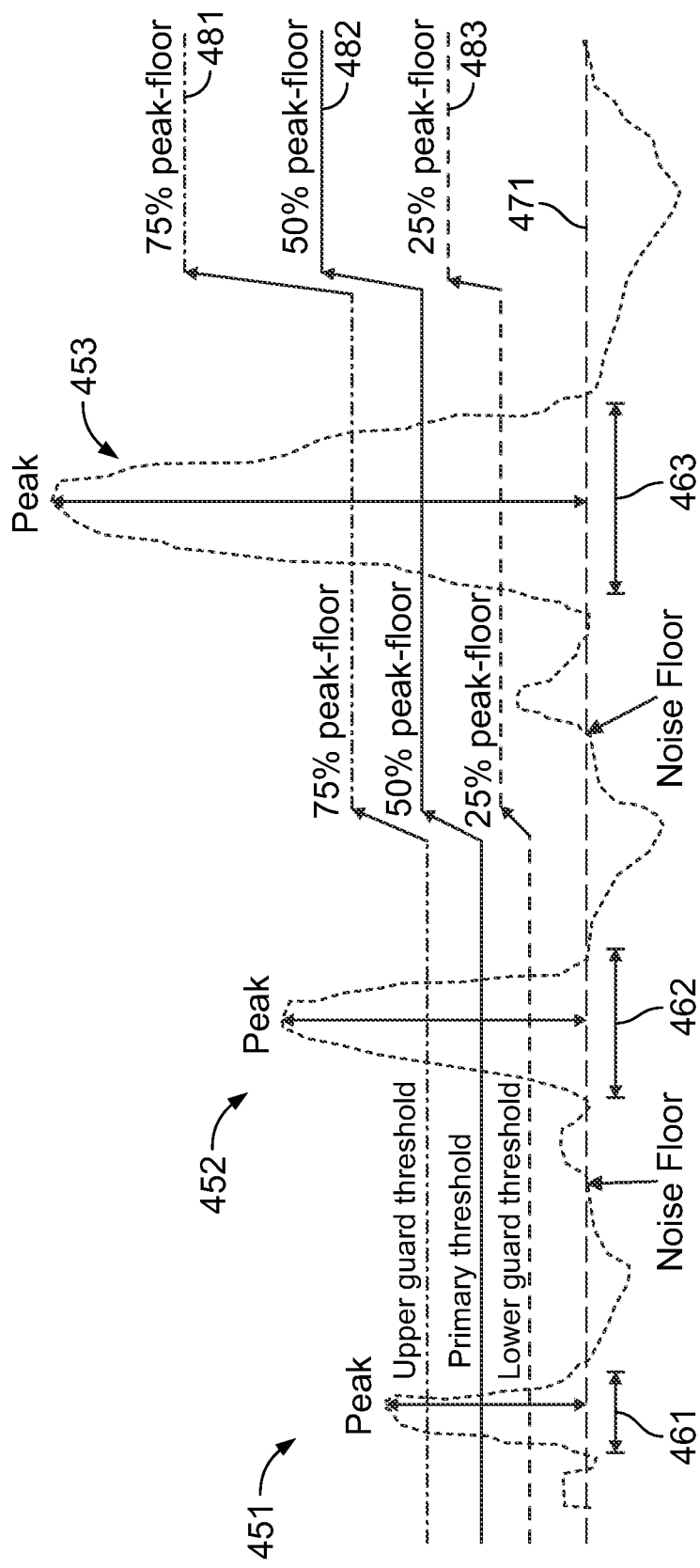
FIG. 8 illustrates the adaptive-sensing process of FIG. 7 when subsequent beats have an increased gain caused by an improved electrode-tissue interface.
Figure 9:
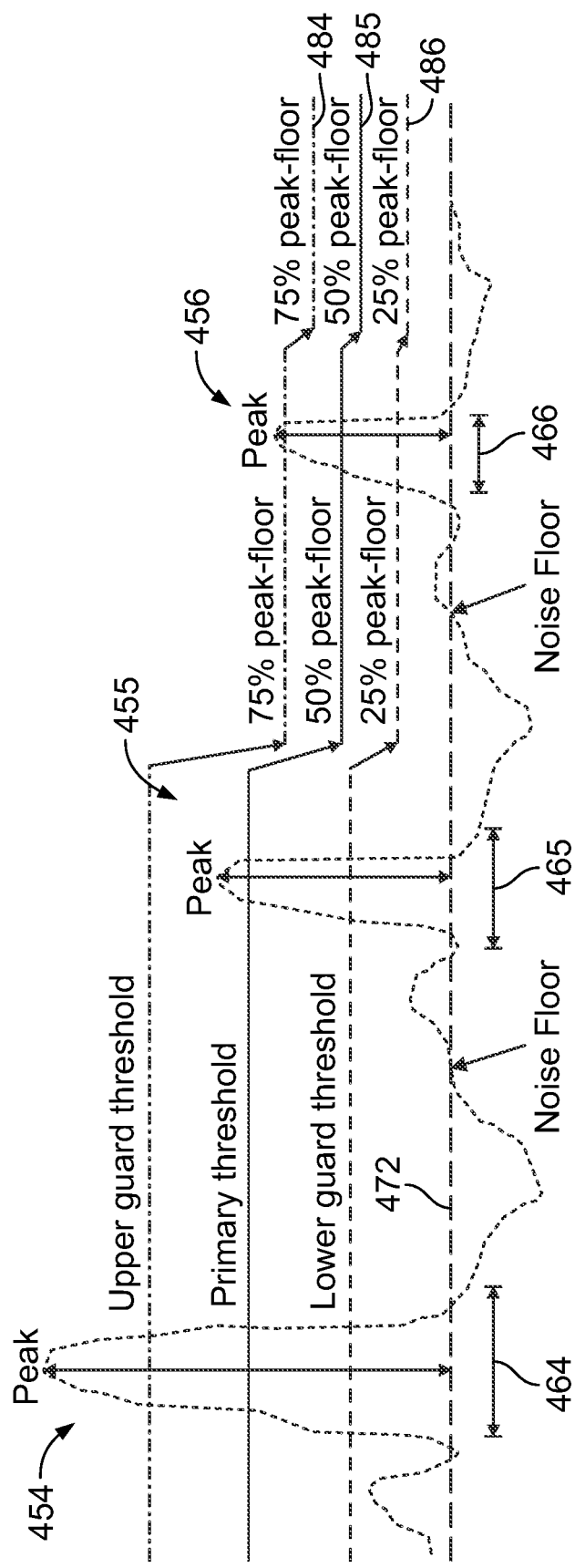
FIG. 9 illustrates the adaptive-sensing process of FIG. 7 in which subsequent beats have a decreased gain caused by an electrode-tissue interface that has worsened.
Figure 10:
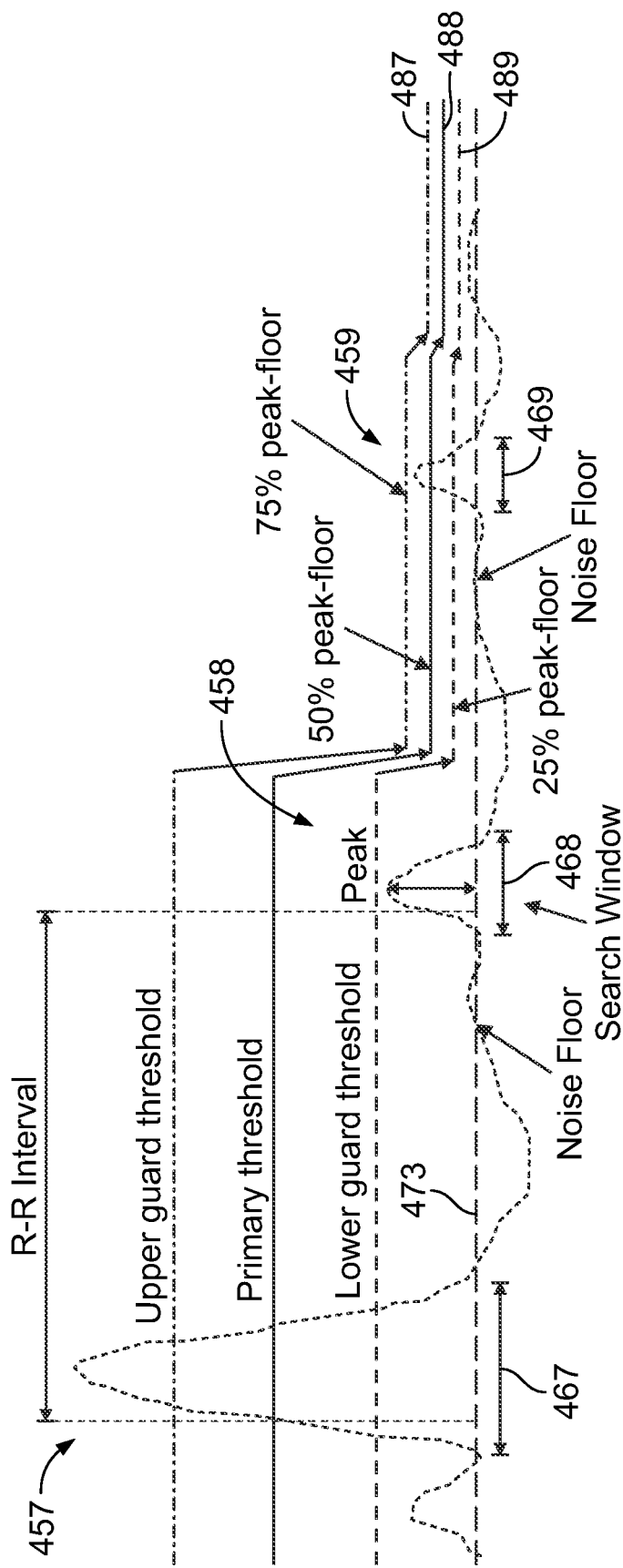
FIG. 10 illustrates the adaptive-sensing process of FIG. 7 in which subsequent beats have a severe drop in signal amplitude.

FIGS. 8-10 illustrate different scenarios confronted by the monitoring system. Each scenario shows three beats-of-interest (BOI), the event prediction windows for each of the BOIs, and the thresholds for the different BOIs. Although FIGS. 8-10 simultaneously illustrate the different parameters for three consecutive beats, it should be understood that the parameters of a subsequent beat are not determined until after analyzing the prior beat.

At 404, the one or more processors of the system determines whether an R-wave was detected within the event prediction window. Depending on the arrangement and configuration of the thresholds, an R-wave may be detected if the CA signals exceed the one or more thresholds in the event prediction window. In the illustrated example, the R-wave is detected if the CA signals exceed at least the lower guard threshold and the primary detection threshold in the event prediction window. The R-wave is also detected if the CA signals exceed the upper guard threshold in the event prediction window in addition to the primary detection threshold and the lower guard threshold.

For example, the first BOI 451 in FIG. 8 is associated with an event prediction window 461 that may be aligned in time to follow a prior R-wave by $X_{MSEC}$. As shown, the CA signals have an amplitude that exceeds each of the lower guard threshold 481, the primary detection threshold 482, and the upper guard threshold 481. Accordingly, the adaptive-sensing process 400 confirms, at 404, that an R-wave was detected and may declare, at 405, to the monitoring system that the R-wave was detected at a designated time within the event prediction window. The adaptive-sensing process 400 may record the R-wave and determine the latest R-R interval based on the current and prior R-waves or a series of R-waved and the like.

At 406, one or more processors may determine whether the R-wave has a PVC morphology. For example, the one or more processors may calculate QRS scores for corresponding QRS complex segments from the CA signals. A variability metric for the QRS scores across a series of beats may be calculated. Correlation coefficients between a QRS complex template and QRS complex segments may also be calculated. The variability metric may be compared to a variability threshold and the correlation coefficients may be compared to a correlation threshold. Such methods and systems are described in U.S. Patent Application Publication No. 2019/0336032, the complete subject matter of which is incorporated herein by reference.

Based on the above analysis, it may be determined whether the CA signals have a PVC morphology. If the CA signals have a PVC morphology, the PVC morphology is communicated to the PVC diagnostics at 407.

The dashed lines at 406 and 407 indicate that determining whether the R-wave has a PVC morphology may be for embodiments in which the sensed event is an R-wave. Sensed events of P-waves and T-waves may not undergo such analysis.

If the CA signals do not have a PVC morphology, the one or more processors of the system may determine whether the noise floor should be changed at 408. More specifically, prior to the R-wave amplitude occurring and after the R-wave amplitude occurring, additional data may be acquired regarding the noise floor. If the new data requires a change in the noise floor, the noise floor is updated at 410. If the new data does not require a change in the noise floor, the characteristics of the R-wave are updated, at 412, and then an event prediction window for the subsequent BOI is calculated.

Returning to the beginning of the adaptive-sensing process, the thresholds for the event prediction window may be confirmed or adjusted at 402. The thresholds may be adjusted based on the number of threshold-crossings (e.g., 0, 1, 2, or 3 threshold-crossings), the amplitude of the prior BOI, and any change in the noise floor. For example, for the BOI 452, the lower guard threshold 483 may be set just above the noise floor 471, the primary detection threshold may be set at a designated point (e.g., 50%) between the amplitude metric and the noise metric, and the upper guard threshold may be positioned above the amplitude. Any margin between the upper guard threshold and the amplitude may be a function of the signal-to-noise ratio.

In the illustrated embodiment of FIGS. 8-10, after each beat, the lower guard thresholds are set at 25% of the difference between the amplitude metric and the noise metric of the prior BOI, the primary detection thresholds are set at 50% of the difference between the amplitude metric and the noise metric of the prior BOI, and the upper guard thresholds are set at 75% of the difference between the amplitude metric and the noise metric of the prior BOI. As described herein, however, the thresholds may be distributed in other manners.

As shown in FIG. 8, the CA signals for the BOI 452 increased in amplitude relative to the CA signals for the BOI 451. The CA signals for the BOI 452 at the event prediction window 462 exceeded the lower guard threshold 483, the primary detection threshold 482, and the upper guard threshold 481. Accordingly, the R-wave will be detected at 404 and declared at 405. The analysis will continue until the process returns to adjusting the thresholds at 402. The thresholds may be increased based upon the detected amplitude of the prior BOI 451. In the illustrated embodiment, the FIG. 9 illustrates a scenario in which one or more subsequent BOIs have a decreased gain caused by an electrode-tissue interface that has worsened. For BOI 455, the CA signals exceed the lower guard threshold 486 and the primary detection threshold 485 for the event prediction window 465. However, the CA signals did not exceed the upper guard threshold. Nevertheless, the R-wave is detected at 404 and declared at 406. Because the CA signals did not exceed the upper guard threshold 484, the thresholds will be decreased prior to the next BOI 486. The lower guard threshold 486, the primary detection threshold 485, and the upper guard threshold 484 are reduced. The amount reduced is based on the amplitude metric of the prior BOI 485 and any change in the noise metric.

If the CA signals for the BOI 455 did not exceed both the primary detection threshold 485 and the upper guard threshold 484 but did exceed the lower guard threshold 486, the R-wave can be detected at 404 and declared at 406. The thresholds can still be decreased prior to the next BOI 486 based on an amplitude metric of the CA signals at the prior BOI 485 and any change in the noise metric.

FIG. 10 illustrates the adaptive-sensing process of FIG. 7 in which one or more subsequent beats have a severe drop in signal amplitude. For BOI 457, the CA signals exceed the lower guard threshold 489, the primary detection threshold 488, and the upper guard threshold 487 for the event prediction window 467. For BOI 458, the CA signals dropped dramatically such that the CA signals did not exceed the lower guard threshold 489, the primary detection threshold 488, nor the upper guard threshold 487 for the event prediction window 468. In other words, none of the thresholds were crossed. In this case, the process 400 can automatically reduce the thresholds for the next BOI 459 by a substantial amount.

Because the CA signals were never detected for the BOI 458, the event prediction window 469 for the BOI 459 may be based on the R-R interval of the prior two beats 457, 458. The amount reduced for each of the thresholds may be a dramatic reduction, such as a 50% reduction.

At 418, one or more processors of the system determine whether the CA signals, for the event prediction window 469, exceed the upper guard threshold 487, at 418, or the primary detection threshold 488, at 420. In either case, if the CA signals exceed the threshold, the R-wave is detected and declared at 405. If the CA signals do not exceed the thresholds, the one or more processors determines whether the CA signals exceed the lower guard threshold 489, at 422. If the CA signals exceed the lower guard threshold 489, at 422, the event morphology is collected for subsequent analysis at 424. At 426, the event morphology from 424 may be analyzed to determine whether the CA signals sufficiently match a sensed event template. For example, correlation coefficients between a sensed event template and the event morphology from 424 may be calculated.

In the case of a severe sudden drop of the CA signals in which all three of the thresholds fail to detect the CA signals, the system may falsely detect asystole if the system continues to use the same sensing thresholds. In such instances, the system (e.g., hardware, firmware, or software) can analyze, also at 426, CA signals from another channel (e.g., primary channel or from noise-floor channel) that may be essentially raw CA signals just above the noise floor. The CA signals that are analyzed may be those CA signals that align with the event prediction window. If the detected amplitude of the CA signals is above the "noise floor+standard deviation," the system can reset the thresholds. For example, at 428, the one or more processors may determine an amplitude and a noise floor using the CA signals from the other channel. At 426, if there is no detected amplitude or if the event morphology does not sufficiently match an event template, the process 400 returns to the beginning, at 402, using the previously used thresholds.

Figure 11:
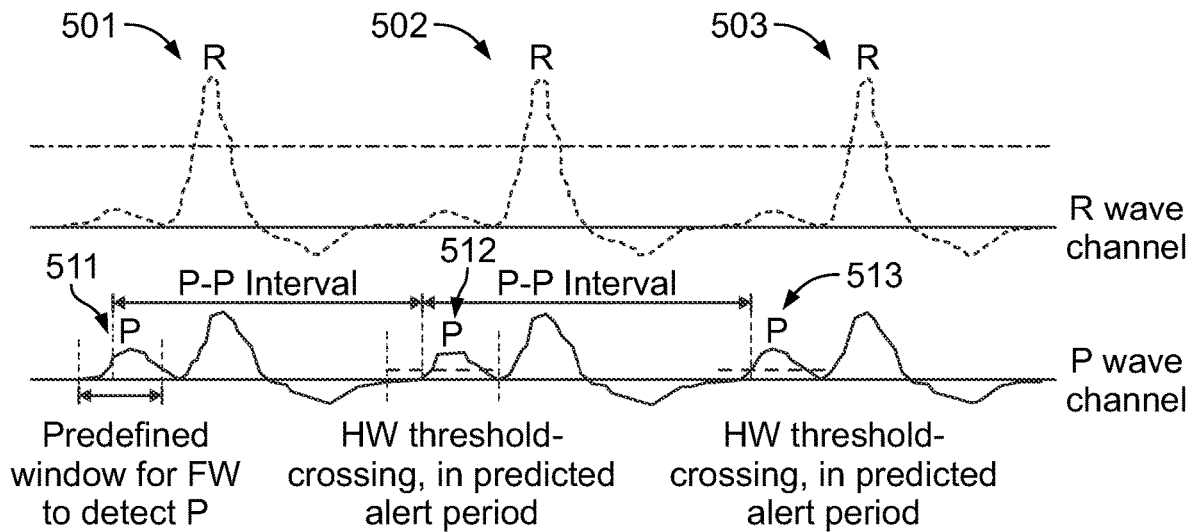
FIG. 11 illustrates one example of an adaptive-sensing process for detecting P-waves or T-waves that may be implemented in accordance with embodiments described herein.

FIG. 11 illustrates P-wave detection process that utilizes the adaptive-sensing process 400 for three beats 501, 502, 503. It can be challenging to reliably detect P-waves, because P-waves and R-waves are acquired together by the same pair of subcutaneous electrodes and the P-waves have a smaller amplitude than R-waves. In some embodiments, the CA signals acquired by the electrodes are provided to two separate channels such that the same CA signals are processed by the two channels. For example, as shown in FIG. 4, the VEGM signals may be provided to the fourth sensing channel 264 and the fifth sensing channel 265. In some embodiments, the fourth sensing channel 264 may have a filtering circuit (e.g., pass band and amplifier) that selectively amplifies the R-wave more than the P-wave. The fifth sensing channel 265 may have a filtering circuit (e.g., pass band and amplifier) that selectively amplifies the P-wave more than the R-wave.

Returning to FIG. 11, embodiments may buffer the fifth sensing channel 265 so that, upon detection and declaration of an R-wave, the threshold-and-peak detector 272 may analyze a search window that is one second prior to the detection of the R-wave. The detector 272 may use a pre-defined threshold to identify P-waves 511, 512, and 513. Consecutive P-waves may be used to calculate P-P intervals.

After the P-P interval distribution is determined, the process 400 may determine an event prediction window (or alert period) in which atrial-sensing hardware for threshold-crossing detection can be enabled to detect the P-wave. The P-wave can then be detected, and two or more thresholds can be adjusted as described above with respect to the process 400 (FIG. 7). Since the fifth sensing channel 265 may still have a greater R-wave amplitude than the P-wave amplitude, the atrial sensing hardware can be disabled outside the alert period.

Figure 12:
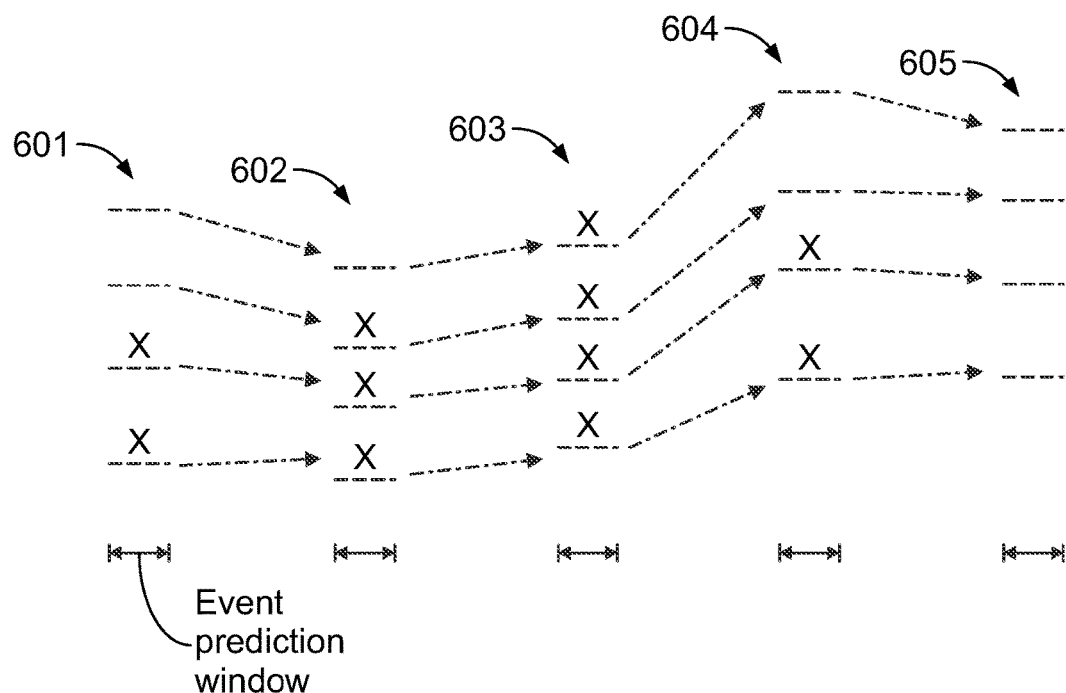
FIG. 12 illustrates an ASC adjustment that utilizes more than three detection thresholds in accordance with embodiments herein.

FIG. 12 illustrates an ASC adjustment that utilizes more than three detection thresholds. In some embodiments, the detection thresholds may be adjusted for each beat without consideration of the amplitude of the prior beat. For example, as shown in FIG. 12, if only two of the detection thresholds are exceeded for beat 601, the detection thresholds may be automatically decreased for the subsequent beat 602. If three of the detection thresholds are exceeded, as shown for beat 602, the detection thresholds may be automatically increased for the subsequent beat 602. If four of the detection thresholds are exceeded, as shown for beat 603, the detection thresholds may be automatically increased for the subsequent beat 604. The adjustment increase to the detection thresholds after the beat 603 may be greater than the increase after the beat 602 because more detection thresholds were exceeded. If two of the detection thresholds are exceeded, as shown for beat 604, the detection thresholds may be automatically decreased for the subsequent beat 605.

In this manner, the detection thresholds may be automatically adjusted without consideration of the amplitude of the sensed event. Nonetheless, the amplitude may be recorded for subsequent analysis.

In some embodiments, a computer implemented method of detecting cardiac activity (CA) signals is provided. Under control of one or more processors configured with specific executable instructions, the method includes determining, for a series of beats, an event prediction window for detecting a sensed event (e.g., R-wave, T-wave, P-wave, and the like) associated with a beat-of-interest (BOI) and whether the CA signals for the BOI exceeds at least one of a primary detection threshold or an upper guard threshold. The upper guard threshold is greater than the primary detection threshold. Responsive to the CA signals of a current BOI exceeding the upper guard threshold within the event prediction window of the current BOI, the method also includes declaring that the sensed event is present within the current BOI, determining the event prediction window for a subsequent BOI, and increasing the primary detection threshold and the upper guard threshold for the subsequent BOI based on a amplitude of the CA signals of the current BOI within the event prediction window. Responsive to the CA signals of the current BOI not exceeding the upper guard threshold within the event prediction window of the current BOI but exceeding the primary detection threshold, the method also includes declaring that the sensed event is present within the current BOI, determining the event prediction window for the subsequent BOI, and decreasing the primary detection threshold and the upper guard threshold for the subsequent BOI based on the amplitude of the CA signals of the current BOI within the event prediction window.

Optionally, the method also includes determining, for the series of beats, whether the CA signals for the BOI exceeds a lower guard threshold, wherein the lower guard threshold being less than the primary detection threshold. Responsive to the CA signals of the current BOI not exceeding the lower guard threshold within the event prediction window of the current BOI, the method also includes declaring that the sensed event is present within the current BOI, determining the event prediction window for the subsequent BOI, and decreasing the lower guard threshold, the primary detection threshold, and the upper guard threshold for the subsequent BOI based on the amplitude of the CA signal for the BOI.

Optionally, the method also includes processing, in parallel, the CA signals through a first channel having the primary detection threshold, a second channel having the upper guard threshold, and a third channel having the lower guard threshold.

Optionally, responsive to the CA signal for the subsequent BOI not exceeding the decreased lower guard threshold, the method also includes analyzing the CA signals within the event prediction window of the subsequent BOI to determine whether a suspected amplitude exists. The method also includes determining that the suspected amplitude of the CA signals within the subsequent event prediction window is statistically significant, thereby confirming that the sensed event is present in the CA signals of the subsequent BOI. The method also includes decreasing the lower guard threshold, the primary detection threshold, and the upper guard threshold for the BOI after the subsequent BOI based on the suspected amplitude determined to be statistically significant.

Optionally, the method also includes processing, in parallel, the CA signals through a first channel having the primary detection threshold, a second channel having the upper guard threshold, a third channel having the lower guard threshold, and a fourth channel having a threshold that is less than the lower guard threshold.

Optionally, the increasing of the primary detection threshold or the decreasing of the primary detection threshold for the subsequent BOI is based on a difference between the amplitude of the current BOI and a noise floor.

Optionally, the increasing of the primary detection threshold or the decreasing of the primary detection threshold for the subsequent BOI is based on a peak-amplitude trend of previous amplitudes.

Optionally, prior to determining, for the series of beats, the event prediction window and whether the CA signals for the BOI exceeds at least one of the primary detection threshold or the upper guard threshold, the method also includes processing, in parallel, the CA signals through a first wave channel and a second wave channel. The first and second wave channels have first and second filtering circuits. The first wave channel amplifies a first wave characteristic-of-interest and the second wave channel amplifies a different second wave characteristic-of-interest.

Optionally, the first wave channel selectively amplifies an R-wave more than a P-wave of a BOI and the second wave channel selectively amplifies the P-wave more than the R-wave of the BOI. The event prediction window is configured to include the P-wave and the primary detection threshold, and the upper guard threshold are applied to the P-wave of the BOI.

Closing

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A computer implemented method for cardiac activity (CA) signals using an implantable medical device (IMD) that includes one or more processors, sensing circuitry, and sense electrodes coupled to the sensing circuitry to define first and second sensing channels, wherein under control of the one or more processors of the IMD that are configured with specific executable instructions, the method comprises:
   detecting the CA signals, over the first and second channels, using the sense electrodes;
   monitoring the CA signals detected by the sense electrodes, for a series of beats, over the first and second sensing channels having different first and second detection thresholds, respectively;
   analyzing the CA signals over the first and second sensing channels utilizing the first and second detection thresholds, respectively, during an event prediction window to detect a presence of sensed events;
   determining amplitudes of the sensed events detected;
   determining whether the CA signals for a current beat of interest (BOI) exceed at least one of a primary detection threshold or an upper guard threshold, the upper guard threshold being greater than the primary detection threshold, wherein the first and second detection thresholds represent the primary detection threshold and the upper guard threshold, respectively;

calculating at least one of an amplitude distribution or amplitude trend for the sensed events detected over the first and second channels; and adjusting at least one of the first or second detection thresholds based on the at least one of the amplitude distribution or amplitude trend.

2. The method of claim 1, wherein, responsive to the CA signals of the current BOI exceeding the upper guard threshold, the method further comprises:

declaring that the sensed event is present within the current BOI; and increasing at least one of the primary detection threshold or the upper guard threshold for a subsequent BOI.

3. The method of claim 2, wherein the increasing the at least one of the primary detection threshold or the upper guard threshold includes increasing the at least one of the primary detection threshold or the upper guard threshold based on an amplitude of the CA signals of the current BOI within the event prediction window.

4. The method of claim 1, wherein, responsive to the CA signals of the current BOI not exceeding the upper guard threshold but exceeding the primary detection threshold, the method further comprises:

declaring that the sensed event is present within the current BOI; and decreasing at least one of the primary detection threshold or the upper guard threshold for a subsequent BOI.

5. The method of claim 1, further comprising:

calculating at least one of an interval distribution or interval trend for events-of-interest from the CA signals; and estimating a time of the event prediction window for detecting the sensed events based on the at least one of the interval distribution or interval trend.

6. The method of claim 1, further comprising at least a third detection threshold, wherein the first, second, and third detection thresholds are distributed within a sensitivity range;

wherein the analyzing the CA signals includes determining whether the CA signals for a current beat of interest (BOI) exceeds the first, second, or third detection thresholds; and wherein the method further comprises increasing or decreasing one or more of the first, second, or third detection thresholds based on a total number of the first, second, or third detection thresholds being exceeded.

7. The method of claim 1, wherein the sensed event is at least one of an R-wave, a P-wave, or a T-wave.

8. The method of claim 1, further comprising processing the CA signals through first and second filtering circuits, the first filtering circuit amplifying a first event-of-interest and the second filtering circuit amplifying a different second event-of-interest.

9. The method of claim 8, wherein the first filtering circuit selectively amplifies an R-wave or T-wave more than a P-wave and the second filtering circuit selectively amplifies the P-wave more than the R-wave or T-wave.

10. A system for detecting cardiac activity (CA) signals with an implantable medical device (IMD), comprising:

sense electrodes configured to detect the CA signals;

sensing circuitry included within the IMD and configured to sense the CA signals detected by the sense electrodes, the sensing circuitry defining first and second sensing channels;

memory to store specific executable instructions;

one or more processors configured to execute the specific executable instructions for:

monitoring the CA signals, for a series of beats, over the first and second sensing channels having different first and second detection thresholds, respectively;

analyzing the CA signals over the first and second sensing channels utilizing the first and second detection thresholds, respectively, during an event prediction window to detect a presence of sensed events;

determining amplitudes of the sensed events detected;

determining whether the CA signals for a current beat of interest (BOI) exceed at least one of a primary detection threshold or an upper guard threshold, the upper guard threshold being greater than the primary detection threshold, wherein the first and second detection thresholds represent the primary detection threshold and the upper guard threshold, respectively;

calculating at least one of an amplitude distribution or amplitude trend for the sensed events detected over the first and second channels; and adjusting at least one of the first or second detection thresholds based on the at least one of the amplitude distribution or amplitude trend.

11. The system of claim 1, wherein, when the CA signals of the current BOI exceed the upper guard threshold, the one or more processors are configured to:

declare that the sensed event is present within the current BOI; and increase at least one of the primary detection threshold or the upper guard threshold for a subsequent BOI.

12. The system of claim 11, wherein the one or more processors are further configured to increase the at least one of the primary detection threshold or the upper guard threshold based on the amplitude of the CA signals of the current BOI within the event prediction window.

13. The system of claim 1, wherein, when the CA signals of the current BOI do not exceed the upper guard threshold but do exceed the primary detection threshold, the one or more processors are configured to:

declare that the sensed event is present within the current BOI; and decrease at least one of the primary detection threshold or the upper guard threshold for a subsequent BOI.

14. The system of claim 10, wherein the one or more processors are configured to:

calculate at least one of an interval distribution or interval trend for events-of-interest from the CA signals; and estimate a time of the event prediction window for detecting the sensed events based on the at least one of the interval distribution or interval trend.

15. The system of claim 10, further comprising at least a third detection threshold, wherein the first, second, and third detection thresholds are distributed within a sensitivity range;

wherein the one or more processors are configured to:

determine whether the CA signals for a current beat of interest (BOI) exceed the first, second, or third detection thresholds; and increase or decrease one or more of the first, second, or third detection thresholds based on a total number of the first, second, or third detection thresholds that are exceeded.

16. The system of claim 10, wherein the sensed event is at least one of an R-wave, a P-wave, or a T-wave.

17. The system of claim 10, further comprising first and second filtering circuits within the first and second sensing channels, the first filtering circuit configured to amplify a first event-of-interest and the second filtering circuit configured to amplify a different second event-of-interest, the first and second events of interest representing different first and second sensed events.

18. The system of claim 17, wherein the first filtering circuit selectively amplifies an R-wave or T-wave more than a P-wave and the second filtering circuit selectively amplifies the P-wave more than the R-wave or the T-wave.

* * * * *